United States Patent
Tomori et al.

(10) Patent No.: US 7,012,147 B2
(45) Date of Patent: Mar. 14, 2006

(54) INDOLINE DERIVATIVE AND PROCESS FOR PRODUCING THE SAME

(75) Inventors: Hiroshi Tomori, Hiratsuka (JP);
Hiroshi Miyamoto, Chigasaki (JP);
Hiroshi Fukuhara, Yokohama (JP);
Katsuhiko Fujimoto, Hiratsuka (JP);
Masakazu Wakayama, Hiratsuka (JP);
Ryoichi Sonobe, Yokohama (JP);
Motoko Miura, Hiratsuka (JP);
Kazuhiko Shimura, Isehara (JP)

(73) Assignee: Sankyo Company, Limited, Tokyo (JP)

( * ) Notice: Subject to any disclaimer, the term of this patent is extended or adjusted under 35 U.S.C. 154(b) by 212 days.

(21) Appl. No.: 10/635,040

(22) Filed: Jul. 31, 2003

(65) Prior Publication Data

US 2004/0058979 A1   Mar. 25, 2004

Related U.S. Application Data

(63) Continuation of application No. PCT/JP02/00804, filed on Feb. 1, 2002.

(30) Foreign Application Priority Data

Feb. 2, 2001   (JP)   ............................... 2001-026374

(51) Int. Cl.
*C07D 209/08*   (2006.01)
(52) U.S. Cl. ...................................... 548/491; 548/490
(58) Field of Classification Search ............... 548/490, 548/491
See application file for complete search history.

(56) References Cited

U.S. PATENT DOCUMENTS

| | | | |
|---|---|---|---|
| 3,679,701 A * | 7/1972 | Hester, Jr. ................... | 548/490 |
| 5,990,150 A | 11/1999 | Matsui et al. | |
| 6,063,806 A | 5/2000 | Kamiya et al. | |
| 6,765,014 B1 * | 7/2004 | Corrie et al. ............... | 514/415 |
| 2002/0055533 A1 * | 5/2002 | Kohama et al. ............ | 514/423 |

FOREIGN PATENT DOCUMENTS

| | | | |
|---|---|---|---|
| EP | 0 782 986 A1 | | 7/1997 |
| EP | 0 866 059 A1 | | 9/1998 |
| JP | 2002047269 A | * | 2/2002 |
| WO | WO 97/12860 A1 | | 4/1997 |
| WO | WO 200272147 A1 | * | 9/2002 |
| WO | WO 2003084572 A1 | * | 10/2003 |
| WO | WO 2004009119 A1 | * | 1/2004 |

OTHER PUBLICATIONS

Kamiya, S., et al., "Bioavailable Acyl-CoA: Cholesterol Acyltransferase Inhibitor with Anti-peroxidative Activity," Chem. Pharm. Bull., vol. 48(6), pp. 817-827 (Jun. 2000), at p. 818, col. 2, lines 16-25 and "Chart 2" (nitration of indolines).*

* cited by examiner

*Primary Examiner*—Kamal A. Saeed
*Assistant Examiner*—Anthony J. Paviglianiti
(74) *Attorney, Agent, or Firm*—Frishauf, Holtz, Goodman & Chick, P.C.

(57) ABSTRACT

The present invention provides novel synthetic intermediates for the production of indoline derivatives, which exhibit excellent ACAT inhibitory activity, and processes for the preparation thereof.

1 Claim, No Drawings

INDOLINE DERIVATIVE AND PROCESS FOR PRODUCING THE SAME

This is a continuation application of International Application No. PCT/JP02/00804 filed Feb. 1, 2002, which is incorporated herein by reference in its entirety.

The present invention relates to novel intermediates for the synthesis of indoline derivatives, which exhibit excellent ACAT inhibitory activity, and to processes for the preparation thereof.

Indoline derivatives of the following general formula (1) [wherein $R^2$ and $R^3$ are the same or different and each represents a lower alkyl group; nOc represents an octyl group; preferred compound of formula (1) is a compound of formula (1a), i.e. wherein $R^2$ and $R^3$ represent both methyl group] have excellent inhibitory activity against acyl-coenzyme A: cholesterol acyltransferase (hereinafter referred to as ACAT), as disclosed in Japanese Patent Number 2968050 (EP 866,059 and U.S. Pat. No. 6,063,806).

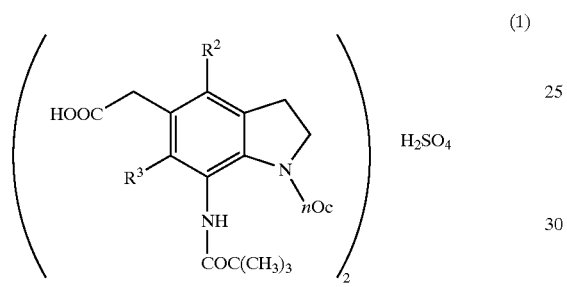

Synthetic intermediates of indoline derivatives of formula (1) and processes for their preparation are disclosed in Japanese Patent Application Publication Number Hei 8-92210 (EP 782,986 and U.S. Pat. No. 5,990,150). In particular, synthetic intermediates of the indoline derivative of formula (1a) and processes for their preparation are described in Example 3(1) and (2) of Japanese Patent Application Publication Number Hei 8-92210 (EP 782,986 and U.S. Pat. No. 5,990,150) as shown in the following scheme.

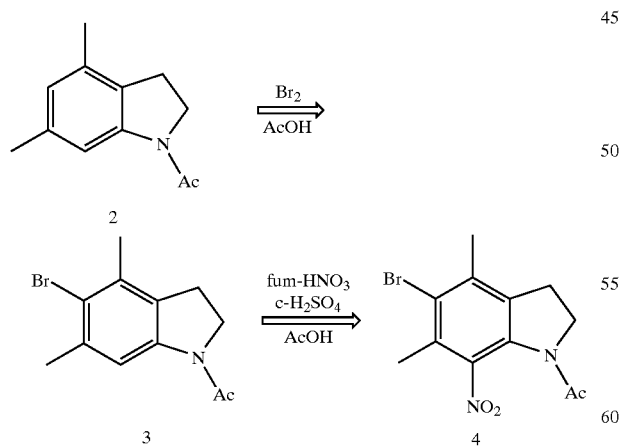

[wherein Ac represents an acetyl group]

The following process for the preparation of the compound of formula (1a) is disclosed in the Examples 3, 4 and 6 in Japanese Patent Number 2968050 (EP 866,059 and U.S. Pat. No. 6,063,806).

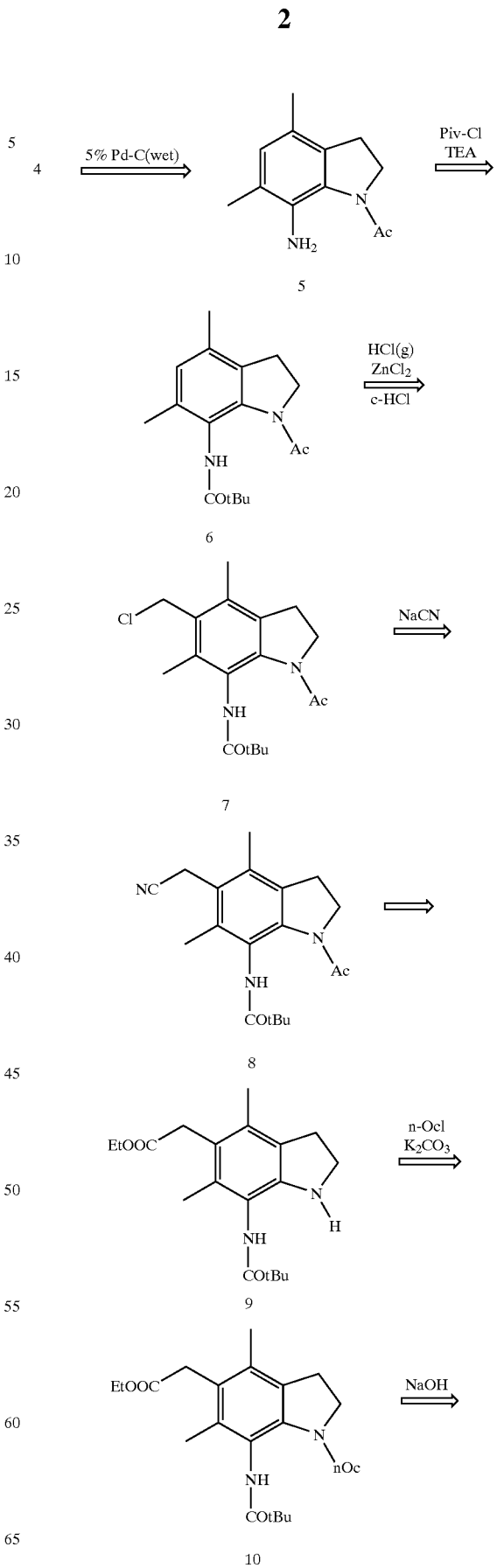

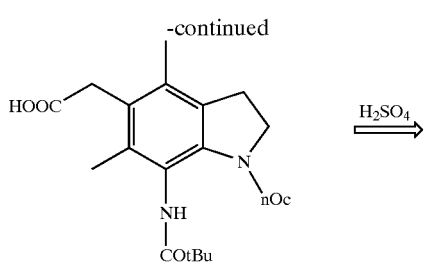

11

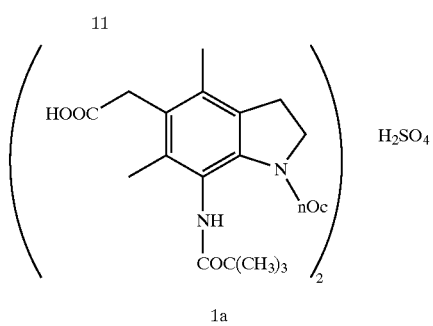

1a

[wherein Et represents an ethyl group; tBu represents a t-butyl group; Ac and nOc have the same meanings as given above].

In the above process for the preparation of the compound of formula (1a), the yield for each step of the reaction is as follows:

the step to compound (3) from compound (2): 83.4%,
the step to compound (4) from compound (3):63.2%,
the step to compound (6) from compound (4): 76.0%,
the step to compound (7) from compound (6): 90.0%,
the step to compound (8) from compound (7): 75.9%,
the step to compound (9) from compound (8): 59.1%,
the step to compound (10) from compound (9): 74.8%,
the step to compound (11) from compound (10): 73.2%
the step to compound (1a) from compound (10): 59.7%, and
the step to compound (1a) from compound (2): 7.2%.

BRIEF DESCRIPTION OF THE INVENTION

The inventors have for many years made great efforts to study synthetic intermediates of indoline derivatives of formula (1), which exhibit excellent ACAT inhibitory activity, and to study processes for their preparation. They have found novel synthetic intermediates of the indoline derivatives of formula (1) and novel processes for their preparation and have completed the invention. The novel preparation process is excellent compared to previous processes, in that:

(1) there is no need to use bromine or sodium cyanide, which have some handling and safety problems in work operation, (2) operation conditions of reactions can be improved, especially, for example, in the nitration process, (3) productivity, such as being able to shorten working time (about ⅔), can be increased, (4) reaction conditions can be greatly relaxed, such as by lowering the concentration of aqueous sodium hydroxide solution in the last step of preparing the carboxylic acid compound, and (5) a high yield of the compound of formula (1) can be obtained (the previous overall yield of the compound of formula (1) from the compound of formula (2) disclosed in the prior art reference was 7.2%, whereas the yield obtained by this invention is 27.3% or more).

The present invention provides novel and useful intermediates for the preparation of indoline derivatives of formula (1) and processes for their preparation.

DETAILED DESCRIPTION OF THE INVENTION

The novel intermediate of the present invention is a compound of general formula (I)

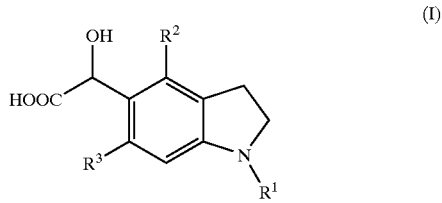

(wherein $R^1$ represents a protective group for the amino group, $R^2$ and $R^3$ are the same or different and each represents a lower alkyl group), a salt or an amide derivative thereof;

or a compound of general formula (II)

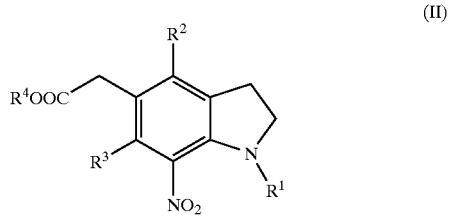

(wherein $R^1$ represents a protective group for the amino group, $R^2$ and $R^3$ are the same or different and each represents a lower alkyl group, $R^4$ represents a hydrogen atom or a protective group for the carboxyl group), a salt or an amide derivative thereof.

On the other hand, a novel process for the preparation of the compound of general formula (I)

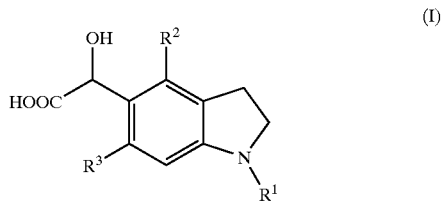

which is a novel synthetic intermediate in the present invention, (wherein $R^1$ represents a protective group for the amino group, $R^2$ and $R^3$ are the same or different and each represents a lower alkyl group) or a salt thereof, comprises the reaction of a compound of general formula (IV)

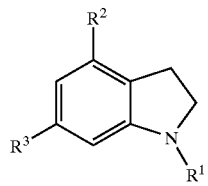

(wherein R¹, R² and R³ have the same meanings as given above) with a compound of general formula (V)

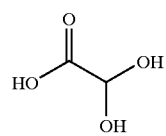

or a salt thereof.

A novel process for the preparation of the compound of general formula (VI')

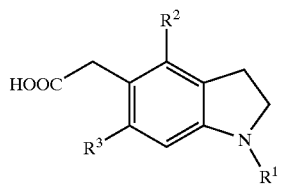

which is a novel synthetic intermediate in the present invention, (wherein R¹ represents a protective group for the amino group, R² and R³ are the same or different and each represents a lower alkyl group) or a salt thereof, comprises the reduction of the hydroxyl group of a compound of general formula (I)

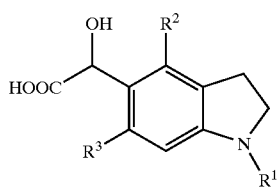

(wherein R¹, R² and R³ have the same meanings given above) or a salt thereof by phosphorous acid and an alkali metal iodide, preferably in an organic acid.

A novel process for the preparation of the compound of general formula (II)

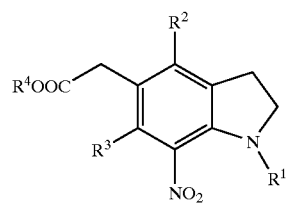

which is a novel synthetic intermediate in the present invention, (wherein R¹ represents a protective group for the amino group, R² and R³ are the same or different and each represents a lower alkyl group, R⁴ represents a hydrogen atom or a protective group for the carboxyl group) or a salt thereof, comprises the nitration of a compound of general formula (VI)

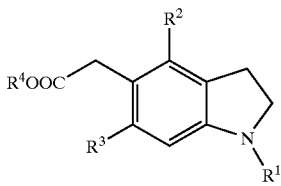

(wherein R¹, R², R³ and R⁴ have the same meanings as given above) or a salt thereof.

A novel process for the preparation of the compound of general formula (VII)

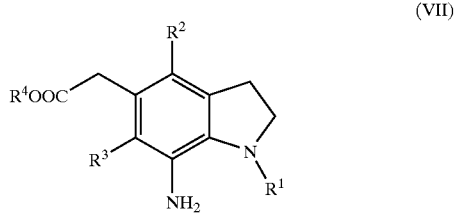

which is a synthetic intermediate in the present invention, (wherein R¹ represents a protective group for the amino group, R² and R³ are the same or different and each represents a lower alkyl group, R⁴ represents a hydrogen atom or a protective group for the carboxyl group) or a salt thereof, comprises the reduction of a compound of general formula (II)

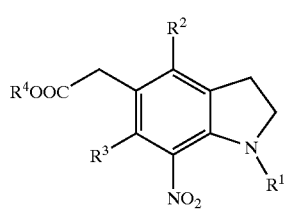

(wherein R¹, R², R³ and R⁴ have the same meanings as given above) or a salt thereof.

A novel process for the preparation of the compound of general formula (VIII)

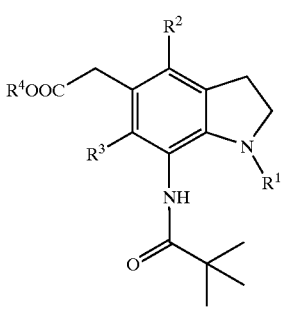

which is a synthetic intermediate in the present invention, (wherein R¹ represents a protective group for the amino group, $R^2$ and $R^3$ are the same or different and each represents a lower alkyl group, $R^4$ represents a hydrogen atom or a protective group for the carboxyl group) or a salt thereof, comprises the pivaloylation of a compound of general formula (VII)

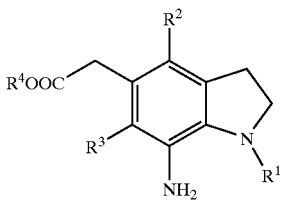

(VII)

(wherein $R^1$, $R^2$, $R^3$ and $R^4$ have the same meanings as given above) or a salt thereof.

A novel process for the preparation of the compound of general formula (III)

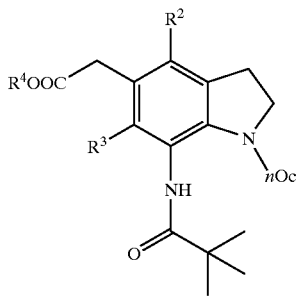

(III)

which is a synthetic intermediate in the present invention, (wherein $R^2$ and $R^3$ are the same or different and each represents a lower alkyl group, $R^4$ represents a hydrogen atom or a protective group for the carboxyl group, nOc represents an octyl group) or a salt thereof, comprises the octylation of a compound of general formula (IX)

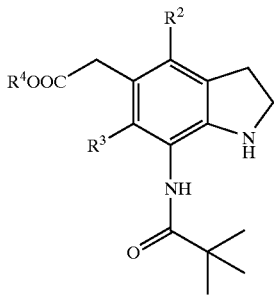

(IX)

(wherein $R^2$, $R^3$ and $R^4$ have the same meanings as given above) or a salt thereof, preferably in a solvent of butyl acetate or xylene and more preferably in the presence of diisopropylethylamine as a base.

The protective group for the amino group in the definition of $R^1$ is a usual protective group for amino groups and includes an "aliphatic acyl group", for example, a $C_1$–$C_{20}$ alkylcarbonyl group such as formyl, acetyl, propionyl, butyryl, isobutyryl, pentanoyl, pivaloyl, valeryl, isovaleryl, octanoyl, lauroyl, myristoyl, tridecanoyl, palmitoyl or stearoyl; a halogeno lower alkylcarbonyl group such as chloroacetyl, dichloroacetyl, trichloroacetyl or trifluoroacetyl; a lower alkoxy-lower alkylcarbonyl group such as methoxyacetyl or an unsaturated alkylcarbonyl group such as (E)-2-methyl-2-butenoyl; an "aromatic acyl group", for example, an arylcarbonyl group such as benzoyl, α-naphthoyl or β-naphthoyl; a halogeno arylcarbonyl group such as 2-bromobenzoyl or 4-chlorobenzoyl; a lower alkylated arylcarbonyl group such as 2,4,6-trimethylbenzoyl or 4-toluoyl; a lower alkoxylated arylcarbonyl group such as 4-anisoyl; a nitrated arylcarbonyl group such as 4-nitrobenzoyl or 2-nitrobenzoyl; a lower alkoxycarbonylated arylcarbonyl group such as 2-(methoxycarbonyl)benzoyl; or an arylated arylcarbonyl group such as 4-phenylbenzoyl; an "alkoxycarbonyl group", for example, a lower alkoxycarbonyl group such as methoxycarbonyl, ethoxycarbonyl, t-butoxycarbonyl or isobutoxycarbonyl; or a lower alkoxycarbonyl group substituted with a halogen(s) or a tri-lower-alkyl-silyl(s) such as 2,2,2-trichloroethoxycarbonyl, 2-trimethylsilylethoxycarbonyl; an "alkenyloxycarbonyl group" such as vinyloxycarbonyl or allyloxycarbonyl; an "aralkyloxycarbonyl group", which may be optionally substituted with one or two substituents selected from lower alkoxy or nitro group, such as benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl; a "silyl group", for example, a tri-lower-alkylsilyl group such as trimethylsilyl, triethylsilyl, isopropyldimethylsilyl, t-butyldimethylsilyl, methyldiisopropylsilyl, methyl-di-t-butylsilyl or triisopropylsilyl; or a tri-lower-alkyl silyl group substituted with one or two aryl groups such as diphenylmethylsilyl, diphenylbutylsilyl, diphenylisopropylsilyl or phenyldiisopropylsilyl; an "aralkyl group" for example, a lower alkyl group substituted with one to three aryl groups such as benzyl, phenethyl, 3-phenylpropyl, α-naphthylmethyl, β-naphthylmethyl, diphenylmethyl, triphenylmethyl, α-naphthyldiphenylmethyl or 9-anthrylmethyl; or a lower alkyl group substituted with one to three aryl group wherein said aryl group is substituted with substituents selected from lower alkyl, lower alkoxy, nitro, halogen or cyano group such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl or piperonyl; an "acyloxyalkyl group" such as ethylcarbonyloxymethyl, pivaloyloxymethyl, dimethylaminoacetyloxymethyl or 1-acetoxyethyl; a "1-(alkoxycarbonyloxy)alkyl group" such as 1-(methoxycarbonyloxy)ethyl, 1-(ethoxycarbonyloxy)ethyl, ethoxycarbonyloxymethyl, 1-(isopropoxycarbonyloxy)ethyl, 1-(t-butoxycarbonyloxy)ethyl, 1-(ethoxycarbonyloxy)propyl or 1-(cyclohexyloxycarbonyloxy)ethyl; a "phthalidyl group"; or a "carbonyloxyalkyl group", for example an oxodioxolenylmethyl group such as 4-methyl-oxodioxolenylmethyl, 4-phenyl-oxodioxolenylmethyl or oxodioxolenylmethyl. Preferred as protective group for the amino group is an aliphatic acyl group, more preferred is a $C_1$–$C_{20}$ alkylcarbonyl group and most preferred as protective group is an acetyl group.

The "lower alkyl group" in the definition of $R^2$ and $R^3$ is a straight or branched chain alkyl group having from 1 to 6 carbon atoms such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl. Preferred as alkyl group is a straight or branched chain alkyl group having from 1 to 4 carbon atoms, more preferred is a methyl or ethyl group and most preferred is a methyl group.

The term "protective group for the carboxyl group" in the definition of $R^4$ refers to a "protective group in chemical reactions" which can be removed by hydrogenolysis, hydrolysis, electrolysis or photolysis. Such a "protective group in chemical reactions" includes a "lower alkyl group" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl; an "alkenyl group" such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, 5-hexenyl; an "alkynyl group" such as ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl, 5-hexynyl; a "halogeno lower alkyl group" such as trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl or 2,2-dibromoethyl; a "hydroxyl lower alkyl group" such as 2-hydroxyethyl, 2,3-dihydroxypropyl, 3-hydroxypropyl, 3,4-dihydroxybutyl or 4-hydroxybutyl; an "aliphatic acyl lower alkyl group" such as acetylmethyl; an "aralkyl group", for example, a "lower alkyl group" substituted with one to three aryl groups such as benzyl, phenethyl, 3-phenylpropyl, α-naphthylmethyl, β-naphthylmethyl, diphenylmethyl, triphenylmethyl, 6-phenylhexyl, α-naphthyldiphenylmethyl or 9-anthrylmethyl, or a "lower alkyl group" substituted with one to three aryl groups wherein said aryl group is substituted with substituents selected from lower alkyl, lower alkoxy, nitro, halogen, cyano or alkoxycarbonyl group such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl, piperonyl or 4-methoxycarbonylbenzyl; or a "silyl group" such as trimethylsilyl, triethylsilyl, isopropyldimethylsilyl, tert-butyldimethylsilyl, methyldiisopropylsilyl, methyl-di-tert-butylsilyl, triisopropylsilyl, methyldiphenylsilyl, isopropyldiphenylsilyl, butyldiphenylsilyl or phenyldiisopropylsilyl. Preferred as protective group for the carboxyl group is a lower alkyl group, more preferred is a straight or branched chain alkyl having from 1 to 4 carbon atoms, still more preferred is a methyl, ethyl or n-propyl group and most preferred as protective group is an ethyl group.

The term "amide" refers to a group which is produced by substitution of a carboxyl group with an amino group wherein said amino group may be optionally substituted with one or two substituents described below. Said substituent includes the "lower alkyl group" described above; an "alkyloxy group", for example, a lower alkoxy group such as methoxy, ethoxy, n-propoxy, isopropoxy, n-butoxy or t-butoxy, a lower alkoxylated lower alkoxy group such as 2-methoxyethoxy or a halogenated lower alkoxy group such as 2,2,2-trichloroethoxy; an "aralkyloxy group", for example, a lower alkoxy group substituted with one to three aryl groups such as benzyloxy, phenethyloxy, 3-phenylpropoxy, α-naphthylmethoxy, β-naphthylmethoxy, diphenylmethoxy, triphenylmethoxy, α-naphthyldiphenylmethoxy or 9-anthrylmethoxy; or a lower alkoxy group substituted with one to three aryl groups wherein said aryl group is substituted with substituents selected from lower alkyl, lower alkoxy, nitro, halogen or cyano group such as 4-methylbenzyloxy, 2,4,6-trimethylbenzyloxy, 3,4,5-trimethylbenzyloxy, 4-methoxybenzyloxy, 4-methoxyphenyldiphenylmethoxy, 2-nitrobenzyloxy, 4-nitrobenzyloxy, 4-chlorobenzyloxy, 4-bromobenzyloxy, 4-cyanobenzyloxy, 4-cyanobenzyldiphenylmethoxy, bis(2-nitrophenyl)methoxy or piperonyloxy; a "hydroxy lower alkyl group" such as hydroxymethyl, 2-hydroxyethyl or 3-hydroxypropyl; an "amino alkyl group" such as 2-aminoethyl or 3-aminopropyl; or an "aryl group which may be optionally substituted with lower alkyl, lower alkoxy or halogen" such as phenyl, 4-tolyl, 4-methoxyphenyl, 4-chlorophenyl or α- or β-naphthyl.

The salt can be obtained by reaction of a compound having a basic group such as an amino group with an acid or by reaction of a compound having an acidic group such as a carboxyl group with a base.

Preferred salts of a compound having a basic group include an inorganic acid salt, for example, a hydrohalogenic acid salt such as hydrofluoric acid salt, hydrochloric acid salt, hydrobromic acid salt or hydroiodic acid salt, nitric acid salt, perchloric acid salt, sulfuric acid salt, or phosphoric acid salt; an organic acid salt, for example, a lower alkanesulfonic acid salt such as methanesulfonic acid salt, trifluoromethanesulfonic acid salt or ethanesulfonic acid salt, an arylsulfonic acid salt such as benzenesulfonic acid salt or p-toluenesulfonic acid salt, acetic acid salt, malic acid salt, fumaric acid salt, succinic acid salt, citric acid salt, ascorbic acid salt, tartaric acid salt, oxalic acid salt or maleic acid salt; or an amino acid salt such as glycine salt, lysine salt, alginine salt, ornitine salt, glutamic acid salt or aspartic acid salt. More preferred salt is a hydrohalogenic acid salt or organic acid salt, still more preferred salt is a hydrohalogenic acid salt or inorganic acid salt and most preferred salt is hydrochloric acid salt or sulfuric acid salt.

Preferred salts of a compound having an acidic group include an alkali metal salt such as sodium salt, potassium salt or lithium salt; an alkaline earth metal salt such as calcium salt or magnesium salt; a metal salt such as aluminum salt, iron salt, zinc salt, copper salt, nickel salt or cobalt salt; an amine salt which includes, for example, an inorganic salt such as ammonium salt or an organic salt such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt or tris(hydroxymethyl)aminomethane salt.

When the compound of the present invention is allowed to stand in contact with the atmosphere, it may absorb water or water may attach to it to form a hydrate. The present invention encompasses such hydrates.

The compound of the present invention may absorb a solvent to form a solvate. The present invention encompasses such solvates.

When the compound of the present invention has asymmetric carbons, each asymmetric carbon is able to have a configuration of R or S. The compound can exist as various stereoisomers due to such asymmetric carbons. The present invention encompasses both individual stereoisomers and mixtures of two or more of them in any ratio.

The processes for the preparation of the synthetic intermediates, salts and amides of the present invention comprise the following reaction scheme:

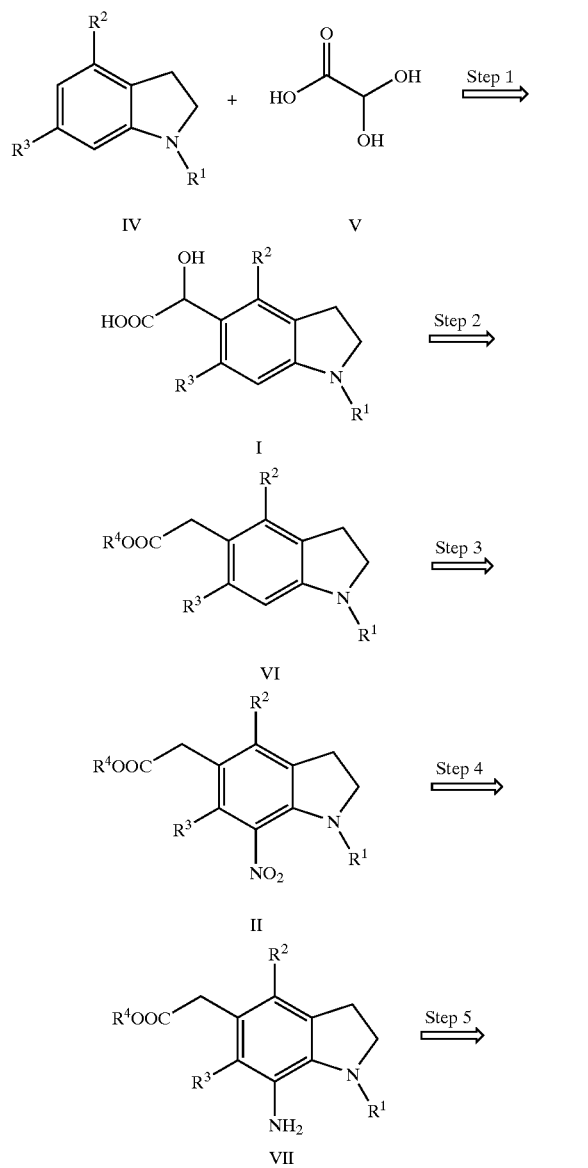

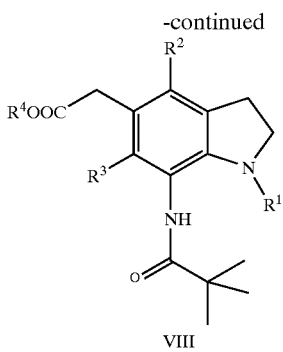

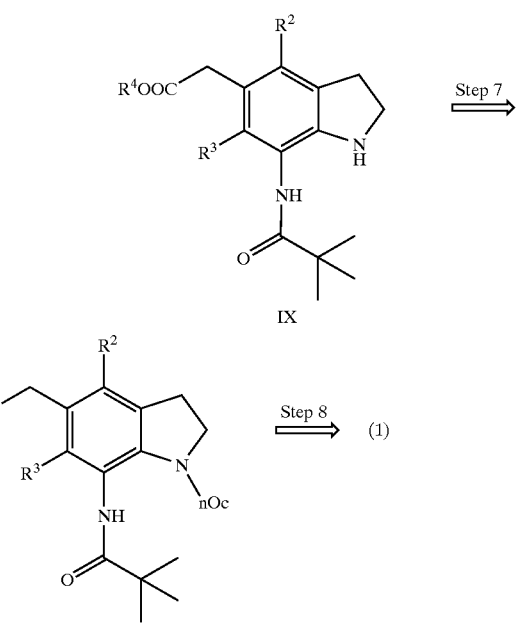

[wherein $R^1$, $R^2$, $R^3$, $R^4$ and nOc are the same meanings as given above].

Step 1

Step 1 is a process for the preparation of a compound of formula (I), which process comprises reacting a compound of formula (IV) (such as the compound of formula (2)) with glyoxylic acid (V) (preferably monohydrate) in the presence of an acid catalyst.

There is no limitation on the acid catalyst used in this process provided that it can be used in usual reactions as an acid catalyst. Preferred acids include a Brønsted acid, for example, an inorganic acid such as hydrochloric acid, hydrobromic acid, sulfuric acid, perchloric acid or phosphoric acid; or an organic acid such as acetic acid, formic acid, oxalic acid, methanesulfonic acid, p-toluenesulfonic acid, camphorsulfonic acid, trifluoroacetic acid or trifluoromethanesulfonic acid. Preferred as acid catalyst is an inorganic acid and most preferred is hydrochloric acid or sulfuric acid.

The solvent used in Step 1 is any usual solvent which has no adverse effect on the reaction. An acidic solvent which acts as an acidic catalyst can be used in Step 1 as a solvent. Preferred as solvent is acetic acid, which acts as an acid catalyst, or water.

The reaction temperature of Step 1 is between 0° C. and 110° C. and preferably between 60° C. and 70° C.

The reaction time of Step 1 depends mainly on the reaction temperature, starting materials, acid catalyst and solvent used in this reaction and usually is in the range of 1 hour to 2 days, preferably from 3 hours to 1 day.

After the reaction of Step 1, the desired compound of formula (I) can be isolated from the reaction mixture by conventional procedure. For example, the desired compound can be obtained by addition of a suitable amount of water to the reaction mixture to form a precipitate and filtration of the crystals. The product thus obtained can, if necessary, be isolated and purified by conventional techniques such as recrystallization, reprecipitation or procedures that are usually used for the isolation and purification of the organic compounds. Examples of procedures mentioned above include adsorption column chromatography using a stationary phase such as silica gel, alumina or florisil composed of magnesium-silica gel; partition column chromatography using a synthetic adsorbent such as Sephadex LH-20 (a product of Pharmacia Co., Ltd.), Amberlite XAD-11 (a product of Rohm & Haas Co., Ltd) or Diaion HP-20 (a product of Mitsubishi Chemical Corporation); ion-exchange chromatography; normal and reversed phase liquid chromatography using silica gel or alkylated silica gel (high performance liquid chromatography is preferred); or a suitable combination of these procedures, and the desired compound can be isolated and purified by eluting with appropriate solvent from the column used.

In the case that it is necessary to separate isomers, each of the isomers can be separated at an appropriate stage such as the end of each step mentioned above or the end of a desired step by performing the suitable separation/purification procedure mentioned above or the combination thereof.

Step 2

Step 2 is a process for the preparation of a compound of formula (VI), which process comprises a reductive removal reaction for the hydroxyl group of a compound of formula (I) and, if necessary, a protection reaction of the carboxyl group of compound of formula (I). The main process of Step 2 can be accomplished in usual manner by conventional reductive reaction of the hydroxyl group. A preferred mode of the reaction is:

(1) catalytic hydrogenation of the hydroxyl group of a compound of formula (I) in a solvent or (2) reduction of the hydroxyl group of a compound of formula (I) by phosphorous acid and an alkali metal iodide.

There is no limitation on the solvent used in the reaction (1) provided that it has no adverse effect on the reaction and that it dissolves the starting materials at least to some extent. Suitable solvents include an alcohol such as methanol, ethanol, n-propanol, isopropanol, n-butanol, isobutanol, t-butanol, isoamylalcohol, diethyleneglycol, glycerin, octanol, cyclohexanol, or methyl cellosolve or an organic acid such as acetic acid. Most suitable as solvent is ethanol or acetic acid.

In addition when an alcohol is used in this reaction as a solvent, a compound of formula (VI) having the $R^4$ group corresponding to said alcohol is obtained (for example, when ethanol is used, a compound of formula (VI) having an ethyl group as the $R^4$ group is obtained and when methanol is used, a compound of formula (VI) having a methyl group as the $R^4$ group is obtained).

The reduction catalyst used in the reaction (1) includes palladium on charcoal, platinum, platinum on charcoal, platinum oxide, palladium hydroxide or Raney nickel and preferably palladium on charcoal.

There is no limitation on the pressure used in the reaction (1) and it is usually in the range of 1 to 10 atmospheres.

The reaction temperature of the reaction (1) is between 30° C. and 90° C. and preferably between 60° C. and 80° C.

The reaction time of the reaction (1) depends mainly on the reaction temperature, starting materials, reduction catalyst and solvent used in this reaction and usually is in the range of 2 hours to 10 hours, preferably from 3 hours to 6 hours.

There is no limitation on the solvent used in the reaction (2) provided that it has no adverse effect on the reaction and that it dissolves the starting materials at least to some extent. Suitable solvents include an organic acid such as acetic acid, formic acid, oxalic acid, methanesulfonic acid, p-toluenesulfonic acid, camphorsulfonic acid, trifluoroacetic acid or trifluoromethanesulfonic acid and a more suitable solvent is acetic acid.

The alkali metal iodide used in the reaction preferably is potassium iodide or sodium iodide and more preferably is potassium iodide.

The reaction temperature of the reaction is between 80° C. and 200° C. and preferably between 90° C. and 180° C.

The reaction time depends mainly on the reaction temperature, starting materials and solvent used in this reaction and usually is in the range of 1 hour to 10 hours, preferably 1.5 hours to 6 hours.

In Step 2 the protection of the carboxyl group, which is an optional process, can be accomplished by method 1 to method 6.

Method 1

The process in Method 1 can be accomplished by reaction of the carboxyl group with a compound of formula $R^4$—X in a solvent in the presence of a base at a temperature in the range of –20° C. to 120° C. (preferably from 0° C. to 80° C.) for a reaction time in the range of 0.5 hours to 10 hours.

In the formula $R^4$—X, $R^4$ has the same meaning as given above, and X represents a leaving group as a nucleophilic residual group, for example, a halogen atom such as chlorine, bromine or iodine; a lower alkanesulfonyloxy group such as methanesulfonyloxy or ethanesulfonyloxy; a halogeno lower alkanesulfonyloxy group such as trifluoromethanesulfonyloxy or pentalluoroethanesulfonyloxy; an arylsulfonyloxy group such as benzensulfonyloxy, p-toluenesulfonyloxy or p-nitrobenzenesulfonyloxy.

$R^4$—X includes, for example, an aliphatic acyloxymethyl halide such as acetoxymethyl chloride, pivaloyloxymethyl bromide or pivaloyloxymethyl chloride; a lower alkoxycarbonyloxyalkyl halide such as ethoxycarbonyloxymethyl chloride, isopropoxycarbonyloxymethyl chloride, 1-(ethoxycarbonyloxy)ethyl chloride or 1-(ethoxycarbonyloxy)ethyl iodide; phthalidiyl halide or (5-methyl-2-oxo-1,3-dioxolen-4-yl)methyl halide.

There is no limitation on the solvent used in Method 1 provided that it has no adverse effect on the reaction and that it dissolves the starting materials at least to some extent. Suitable solvents include an aliphatic hydrocarbon such as hexane or heptane; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone, methyl ethyl ketone, methyl isobutyl ketone, isophorone or cyclohexanone; a nitrile such as acetonitrile or isobutyronitrile; or an amide such as formamide, N,N-dimethylformamide, N,N-dimethylacetoamide, N-methyl-2-pyrrolidone, N-methylpyrrolidinone or hexamethylphosphoric triamide.

There is no limitation on the base used in Method 1 provided that it can be used in usual manner as a base. Suitable bases include an inorganic base, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide, barium hydroxide or lithium hydroxide; an alkali metal fluoride such as sodium fluoride or potassium fluoride; an alkali metal alkoxide such as sodium methoxide, sodium ethoxide, potassium methoxide, potassium ethoxide, potassium tert-butoxide or lithium methoxide; an alkali metal mercaptide such as sodium methylmercaptide or sodium ethylmercaptide; an organic base such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, 1,5-diazabicyclo[4.3.0]non-5-ene or 1,4-diazabicyclo [2.2.2]octane (DABCO) or 1,8-diazabicyclo[5.4.0]undec-7-en (DBU); or an organometallic base such as butyl lithium, lithium diisopropyl amide or lithium bis(trimethylsilyl)amide.

Method 2

The process in Method 2 can be accomplished by reaction of the compound having the carboxyl group with a compound of formula $R^4$—OH [wherein $R^4$ has the same meanings as given above] using a coupling reagent in a solvent in the presence or absence of a base.

The coupling reagent used in Method 2 is:

(i) a combination of an ester of phosphoric acid such as diethylphosphoryl cyanide, diphenylphosphoryl azide or diethyl cyanophosphonate and a base as described below;

(ii) a carbodiimide such as 1,3-dicyclohexylcarbodiimide, 1,3-diisopropylcarbodiimide or 1-ethyl-3-(3-dimethylaminopropyl) carbodiimide; a combination of the carbodiimide given above and a base as described below; a combination of the carbodiimide given above and an N-hydroxy compound such as N-hydroxysuccinimide, 1-hydroxybenzotriazole or N-hydroxy-5-norbornen-2,3-dicarboximide;

(iii) a combination of a disulfide such as 2,2'-dipyridyl disulfide or 2,2'-dibenzothiazolyl disulfide and a phosphine such as triphenylphosphine or tributylphosphine;

(iv) a carbonate such as N,N'-disuccinimidyl carbonate, di-2-pyridyl carbonate or S,S'-bis(1-phenyl-1H-tetrazol-5-yl)dithiocarbonate;

(v) a phosphonic chloride such as N,N'-bis(2-oxo-3-oxazolidinyl)phosphinic chloride;

(vi) an oxalate such as N,N'-disuccinimidyl oxalate, N,N'-diphthalimide oxalate, N,N'-bis(5-norbornen-2,3-dicarboximidyl)oxalate, 1,1'-bis(benzotriazolyl)oxalate, 1,1'-bis(6-chlorobenzotriazolyl)oxalate or 1,1'-bis(6-trifluoromethylbenzotriazolyl)oxalate;

(vii) a combination of the phosphine given above and an ester of azodicarboxylic acid such as diethyl azodicarboxylate or 1,1'-(azodicarbonyl)dipiperidine or an azodicarboxyamide; a combination of the phosphine given above and a base as described below;

(viii) an N-lower alkyl-5-arylisoxazolium-3'-sulfonate such as N-ethyl-5-phenylisoxazolium-3'-sulfonate;

(ix) a diheteroaryl diselenide such as di-2-pyridyl diselenide;

(x) an arylsulfonyl triazolide such as p-nitrobenzenesulfonyl triazolide;

(xi) a 2-halo-1-lower alkylpyridinium halide such as 2-chloro-1-methylpyridinium iodide;

(xii) an imidazole such as 1,1'-oxalyldiimidazole or N,N'-carbonyldiimidazole;

(xiii) a 3-lower alkyl-2-halo-benzothizolium fluoroborate such as 3-ethyl-2-chlorobenzothiazolium fluoroborate;

(xiv) a 3-lower alkyl-benzothiazol-2-selone such as 3-methylbenzothiazol-2-selone;

(xv) a phosphate such as phenyl dichlorophosphate or an ester of polyphosphate;

(xvi) a halosulfonyl isocyanate such as chlorosulfonyl isocyanate;

(xvii) a halosilane such as trimethylsilyl chloride or triethylsilyl chloride;

(xviii) a combination of a lower alkanesulfonyl halide such as methanesulfonyl chloride and a base as described below;

(xix) N,N,N',N'-tetra-lower alkyl-haloformamidium chloride such as N,N,N',N'-tetra-methylchloroformamidium chloride.

Preferred as coupling reagent is a carbodiimide, a combination of a phosphine and an ester of azodicarboxylic acid or an azodicarboxyamide.

There is no limitation on the solvent used in Method 2 provided that it has no adverse effect on the reaction and that it dissolves the starting materials at least to some extent. Suitable solvents include an aliphatic hydrocarbon such as hexane or heptane; an aromatic hydrocarbon such as benzene, toluene or xylene; a halogenated hydrocarbon such as methylene chloride, chloroform, carbon tetrachloride, dichloroethane, chlorobenzene or dichlorobenzene; an ester such as ethyl formate, ethyl acetate, propyl acetate, butyl acetate or diethyl carbonate, an ether such as diethyl ether, diisopropyl ether, tetrahydrofuran, dioxane, dimethoxyethane or di(ethylene glycol)dimethyl ether; a nitrile such as acetonitrile or isobutyronitrile; or an amide such as formamide, N,N-dimethylformamide, N,N-dimethylacetoamide, N-methyl-2-pyrrolidone, N-methylpyrrolidinone or hexamethylphosphoric triamide.

There is no limitation on the base used in Method 2 provided that it can be used in usual manner as a base. Suitable bases include an organic base such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline or N,N-diethylaniline.

In Method 2, a catalytic amount of 4-(N,N-dimethylamino)pyridine or 4-pyrrolidinopyridine can be used in combination with another base. In the coupling reaction, a dehydrating agent such as a molecular sieve; a quaternary ammonium salt such as benzyltriethylammonium chloride or tetrabutylammonium chloride; a crown ether such as dibenzo-18-crown-6; or a trapping agent of acid such as 3,4-dihydro-2H-pyrido[1,2-a]pyrimidin-2-one can be used in order to conduct the reaction effectively.

The reaction temperature is between −20° C. and 80° C. and preferably between 0° C. and room temperature.

The reaction time depends mainly on the reaction temperature, starting materials, reagents and solvent used in this reaction and usually is in the range of 10 minutes to 3 days, preferably 30 minutes to 1 day.

Method 3

Method 3 is a process for the preparation of a compound having a lower alkyl group as a protective group of the carboxyl group. The process can be accomplished by reaction of a compound having a carboxyl group with an alcohol in a solvent in the presence of an acid catalyst at a temperature in the range of 0° C. to 100° C. (preferably 20° C. to 60° C.) for a reaction time in the range of 10 minutes to 24 hours (preferably 15 minutes to 12 hours).

There is no limitation on the solvent used in Method 3 provided that it has no adverse effect on the reaction and that it dissolves the starting materials at least to some extent. Suitable solvents include the same alcohol used as a reagent of this reaction, an aliphatic hydrocarbon such as hexane or heptane; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone, methyl ethyl ketone, methyl isobutyl ketone, isophorone or cyclohexanone; a nitrile such as acetonitrile or isobutyronitrile; or an amide such as formamide, N,N-dimethylformamide, N,N-dimethylacetoamide, N-methyl-2-pyrrolidone, N-methylpyrrolidinone or hexamethylphosphoric triamide. More suitable as solvent is the same alcohol used as a reagent of this reaction.

There is no limitation on the acid catalyst used in Method 3 provided that it can be used in usual manner as an acid catalyst. Suitable acid catalysts include a Brφnsted acid, for example, an inorganic acid such as hydrogen chloride, hydrobromic acid, sulfuric acid, perchloric acid or phosphoric acid; or an organic acid such as acetic acid, formic acid, oxalic acid, methanesulfonic acid, para-toluenesulfonic acid, trifluoroacetic acid or trifluoromethanesulfonic acid; a Lewis acid such as boron trichloride, boron trifluoride or boron tribromide; or an acidic ion-exchange resin. More suitable as acid catalyst is an inorganic acid and most suitable is hydrogen chloride.

The alcohol used in Method 3 as a reagent is methanol, ethanol, propanol or butanol.

Method 4

The process in Method 4 can be accomplished by:

(i) reaction of a compound having a carboxyl group with a halogenating reagent (for example phosphorus pentachloride, thionyl chloride or oxalyl chloride) at a temperature at room temperature for a reaction time in the range of 30 minutes to 5 hours to give an acid halide, or by (ii) reaction of a compound having a carboxyl group with an ester of chloroformic acid such as methyl chloroformate or ethyl chloroformate in the presence of an organic base such as triethylamine to give an acid anhydride, followed by reaction of said acid halide or acid anhydride with an alcohol (when tert-butyl ester is prepared, potassium tert-butoxide is used) in an inert solvent in the presence of a base (for example triethylamine) at −10° C. to 150° C. (preferably room temperature) for 10 minutes to 15 hours (preferably 30 minutes to 10 hours).

There is no limitation on the solvent used in Method 4 provided that it has no adverse effect on the reaction and that it dissolves the starting materials at least to some extent. Suitable solvents include an aromatic hydrocarbon such as benzene, toluene or xylene; a halogenated hydrocarbon such as methylene chloride or chloroform; an ester such as ethyl acetate or propyl acetate; an ether such as diethyl ether, tetrahydrofuran, dioxane or dimethoxyethane; or a nitrile such as acetonitrile.

Method 5

The process in Method 5 can be accomplished by reaction of a compound having a carboxyl group with a diazoalkane such as diazomethane or diazoethane (a solution of diazoalkane in ether) at room temperature (in some cases, if necessary, the reaction may be conducted by heating).

Method 6

Method 6 is a process for the preparation of a compound having a lower alkyl group as a protective group of the carboxyl group. The process can be accomplished by reaction of a compound having a carboxyl group with a dialkyl sulfate such as dimethyl sulfate or diethyl sulfate by conventional procedure.

After the reaction of Step 2, the desired compound of formula (VI) can be isolated from the reaction mixture by conventional procedure. For example, the reaction mixture is neutralized appropriately or precipitates, if present, are removed by filtration, and the neutralized reaction mixture or the filtrate of the reaction mixture is partitioned between an organic solvent such as ethyl acetate that is immiscible with water and water or the like. The separated organic layer containing the desired compound is washed with water, dried over anhydrous magnesium sulfate or the like and concentrated to give the desired product.

The product thus obtained can, if necessary, be isolated and purified by conventional techniques such as recrystallization, reprecipitation or procedures that are usually used for the isolation and purification of the organic compounds. Examples of procedures mentioned above include adsorption column chromatography using a stationary phase such as silica gel, alumina or florisil composed of magnesium-silica gel; partition column chromatography using a synthetic adsorbent such as Sephadex LH-20 (a product of Pharmacia Co., Ltd.), Amberlite XAD-11 (a product of Rohm & Haas Co., Ltd) or Diaion HP-20 (a product of Mitsubishi Chemical Corporation); ion-exchange chromatography; normal and reversed phase liquid chromatography using silica gel or alkylated silica gel (high performance liquid chromatography is preferred); or a suitable combination of these procedures, and the desired compound can be isolated and purified by eluting with appropriate solvent from the column used.

In the case that it is necessary to separate isomers, each of the isomers can be separated at an appropriate stage such as the end of each step mentioned above or the end of a desired step by performing the suitable separation/purification procedure mentioned above or the combination thereof.

Step 3

Step 3 is a process for the preparation of a compound of formula (II), which process comprises a nitration reaction of the 7-position of a compound of formula VI in a solvent.

There is no limitation on the nitration reaction provided that it can be used in usual manner for nitration. Preferred as nitration reaction is a method using nitric acid, sodium nitrate or fuming nitric acid as nitrating agent and more preferably using fuming nitric acid.

There is no limitation on the solvent used in Step 3 provided that it has no adverse effect on the reaction. Suitable as solvent is an acid such as acetic acid, sulfuric acid or a mixture of acetic acid and sulfuric acid and more suitable is a mixture of acetic acid and sulfuric acid.

The reaction temperature of Step 3 is between −20° C. and 30° C. and preferably between −10° C. and 20° C.

The reaction time of Step 3 depends mainly on the reaction temperature, starting materials and solvent used in this reaction and usually is in the range of 0.5 hours to 5 hours, preferably 1 hour to 3 hours.

After the reaction of Step 3, the desired compound of formula (II) can be isolated from the reaction mixture by conventional procedure. For example, the reaction mixture is neutralized appropriately or precipitates, if present, are removed by filtration, and the neutralized reaction mixture or the filtrate of the reaction mixture is partitioned between an organic solvent such as ethyl acetate that is immiscible with water and water or the like. The separated organic layer containing the desired compound is washed with water, dried over anhydrous magnesium sulfate or the like and concentrated to give the desired product.

The product thus obtained can, if necessary, be isolated and purified by conventional techniques such as recrystallization, reprecipitation or procedures that are usually used for the isolation and purification of the organic compounds. Examples of the procedures mentioned above include adsorption column chromatography using a stationary phase such as silica gel, alumina or florisil composed of magnesium-silica gel; partition column chromatography using a synthetic adsorbent such as Sephadex LH-20 (a product of Pharmacia Co., Ltd.), Amberlite XAD-11 (a product of Rohm & Haas Co., Ltd) or Diaion HP20 (a product of Mitsubishi Chemical Corporation); ion-exchange chromatography; normal and reversed phase liquid chromatography using silica gel or alkylated silica gel (high performance liquid chromatography is preferred); or a suitable combination of these procedures, and the desired compound can be isolated and purified by eluting with appropriate solvent from the column used.

In the case that it is necessary to separate isomers, each of the isomers can be separated at an appropriate stage such as the end of each step mentioned above or the end of a desired step by performing the suitable separation/purification procedure mentioned above or the combination thereof.

Step 4

In Step 4, a compound (VII) is prepared by reducing the nitro group of compound (II) in a solvent.

There is no limitation on the solvent used in the reaction provided that it has no adverse effect on the reaction and dissolves the starting materials at least to some extent. Examples of preferable solvents include an ester such as ethyl formate, ethyl acetate, propyl acetate, butyl acetate or diethyl carbonate; an alcohol such as methanol, ethanol, n-propanol, isopropanol, n-butanol, isobutanol, t-butanol, isoamyl alcohol, diethylene glycol, glycerol, octanol, cyclohexanol or methyl cellosolve; or a mixture of solvents thereof. Of these solvents, ethyl acetate, ethanol or mixtures of solvents mentioned above are more preferred.

There is no limitation on the reduction procedure used in the reaction above provided that it is usually used, but catalytic hydrogenation is preferable.

Examples of reduction catalysts used in the catalytic hydrogenation include palladium on charcoal, platinum, platinum on charcoal, platinum oxide, palladium hydroxide and Raney nickel, and palladium on charcoal is more preferred.

There is no limitation on the pressure in the catalytic hydrogenation, but the catalytic hydrogenation is usually carried out at a pressure of from 1 to 10 atmospheres.

The reaction temperature is usually between 20° C. and 80° C., and is preferably from 40° C. to 60° C.

The reaction time depends mainly on the reaction temperature, starting materials and nature of the solvent used in the reaction. The reaction time is usually from 0.5 to 10 hours, and is preferably from 1 to 5 hours.

After the reaction is completed, the compound (VII) that is the desired product of this reaction is isolated from the reaction mixture using conventional techniques.

For example, the reaction mixture is neutralized appropriately or precipitates, if present, are removed by filtration, and the neutralized reaction mixture or the filtrate of the reaction mixture is partitioned between an organic solvent such as ethyl acetate that is immiscible with water and water or the like. The separated organic layer containing the desired compound is washed with water, dried over anhydrous magnesium sulfate or the like and concentrated to give the desired product.

The product thus obtained can, if necessary, be isolated and purified by conventional techniques such as recrystallization, reprecipitation or procedures that are usually used for the isolation and purification of the organic compounds. Examples of the procedure mentioned above include adsorption column chromatography using a stationary phase such as silica gel, alumina or florisil composed of magnesium-silica gel; partition column chromatography using a synthetic adsorbent such as Sephadex LH-20 (a product of Pharmacia Co., Ltd.), Amberlite XAD-11 (a product of Rohm & Haas Co., Ltd) or Diaion HP-20 (a product of Mitsubishi Chemical Corporation); ion-exchange chromatography; normal and reversed phase liquid chromatography using silica gel or alkylated silica gel (high performance liquid chromatography is preferred); or a suitable combination of these procedures, and the desired compound can be isolated and purified by eluting with appropriate solvent from the column used.

In the case that it is necessary to separate isomers, each of the isomers can be separated at an appropriate stage such as the end of each step mentioned above or the end of a desired step by performing the suitable separation/purification procedure mentioned above or the combination thereof.

Step 5

In Step 5, a compound (VIII) is prepared by conducting a pivaloylation of the amino group of compound (VII) in the presence of a base in a solvent.

There is no limitation on the reagent for pivaloylation used in the reaction provided that it is usually used in pivaloylation reactions. Examples of preferable reagents used in this reaction include a pivaloyl halide such as pivaloyl chloride and pivalic anhydride. Of these reagents, pivaloyl halide is more preferred, and pivaloyl chloride is most preferred.

There is no limitation on the base used in the reaction provided that it is usually used as a base in organic chemistry. Examples of preferable bases include an alkali metal hydroxide such as sodium hydroxide, potassium hydroxide, barium hydroxide or lithium hydroxide; and an organic amine such as N-methylmorpholine, triethylamine, tripropylamine, tributylamine, diisopropylamine, diisopropylethylamine, dicyclohexylamine, N-methylpiperidine, pyridine, 4-pyrrolidinopyridine, picoline, 4-(N,N-dimethylamino)pyridine, 2,6-di-t-butyl-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU). The organic bases are more preferred, and diisopropylethylamine or triethylamine is most preferred.

There is no limitation on the solvent used in the reaction provided that it has no adverse effect on the reaction and dissolves the starting materials at least to some extent. Examples of preferable solvents include a halogenated hydrocarbon such as dichloromethane, chloroform, carbon tetrachloride, dichloroethane, chlorobenzene or dichlorobenzene; an ester such as ethyl formate, methyl acetate, ethyl acetate, propyl acetate, butyl acetate or diethyl carbonate; a nitrile such as acetonitrile or isobutyronitrile; and an alcohol such as methanol, ethanol, n-propanol, isopropanol, n-butanol, isobutanol, t-butanol, isoamyl alcohol, diethylene glycol, glycerol, octanol, cyclohexanol or methyl cellosolve. Of these solvents, a halogenated hydrocarbon or an alcohol is more preferred, and dichloromethane or ethanol is most preferred.

The reaction temperature is usually between −10° C. and 20° C., and is preferably between 0° C. and 10° C.

The reaction time depends mainly on the reaction temperature, starting materials and base or solvent used in the reaction. The reaction time is usually from 0.5 to 4 hours, and is preferably from 0.5 to 2 hours.

After the reaction is completed, the compound (VIII) that is the desired product of this reaction is isolated from the reaction mixture using conventional techniques.

For example, the reaction mixture is neutralized appropriately or precipitates, if present, are removed by filtration, and the neutralized reaction mixture or the filtrate of the reaction mixture is partitioned between an organic solvent such as ethyl acetate that is immiscible with water and water or the like. The separated organic layer containing the desired compound is washed with water, dried over anhydrous magnesium sulfate or the like and concentrated to give the desired product.

The product thus obtained can, if necessary, be isolated and purified by conventional techniques such as recrystallization, reprecipitation or procedures that are usually used for the isolation and purification of the organic compounds. Examples of the procedure mentioned above include adsorption column chromatography using a stationary phase such as silica gel, alumina or florisil composed of magnesium-silica gel; partition column chromatography using a synthetic adsorbent such as Sephadex LH-20 (a product of Pharmacia Co., Ltd.), Amberlite XAD-11 (a product of Rohm & Haas Co., Ltd.) or Diaion HP-20 (a product of Mitsubishi Chemical Corporation); ion-exchange chromatography; normal and reversed phase liquid chromatography using silica gel or alkylated silica gel (high performance liquid chromatography is preferred); or a suitable combination of these procedures, and the desired compound can be isolated and purified by elution with appropriate solvent from the column used.

In the case that it is necessary to separate isomers, each of the isomers can be separated at an appropriate stage such as the end of each step mentioned above or the end of a desired step by performing the suitable separation/purification procedure mentioned above or the combination thereof.

Step 6

In Step 6, a compound (IX) is prepared by removing the amino-protective group, $R^1$, of the compound (VIII) in a solvent.

The procedures for removing the $R^1$ group depend on the nature of the protective group used, but the removal of the protective group is generally carried out according to procedures publicly known in the art as described below.

Where the $R^1$ group is a silyl group, the deprotection reaction is usually carried out by treating with a compound that generates a fluorine anion, such as tetrabutylammonium fluoride.

There is no limitation on the solvent used in the above-mentioned reaction provided that it has no adverse effect on the reaction. Examples of preferable solvents include an ether such as tetrahydrofuran or dioxane.

There is no limitation on the reaction temperature and the reaction time is not particularly limited. However, the deprotection reaction is usually carried out at room temperature for a period of from 10 to 18 hours.

Where the $R^1$ group is an aliphatic acyl group, an aromatic acyl group or an alkoxycarbonyl group, those can be removed by treating with an acid or a base in the presence of a solvent.

There is no limitation on the acid used in the above-mentioned reaction provided that it is usually used as an acid and has no adverse effect on the reaction. Examples of preferable acids include an inorganic acid such as hydrochloric acid, sulfuric acid, phosphoric acid, hydrobromic acid, hydrogen chloride or hydrogen bromide. Hydrogen chloride is most preferred.

There is no limitation on the base used in the above-mentioned reaction provided that it has no adverse effect on the structural moieties other than the protective group. Examples of preferable bases include an alkali metal alkoxide such as sodium methoxide, sodium ethoxide, potassium methoxide, potassium ethoxide, potassium t-butoxide, lithium methoxide or lithium ethoxide; an alkali metal carbonate such as sodium carbonate, potassium carbonate or lithium carbonate; an alkali metal hydroxide such as sodium hydroxide, potassium hydroxide or lithium hydroxide; or an ammonia solution such as ammonia aqueous solution or concentrated ammonia solution in methanol. An alkali metal alkoxide is most preferred.

There is no limitation on the solvent used in the above-mentioned reaction provided that it is usually used in hydrolysis reactions or solvolysis reactions. Examples of preferable solvents include water; an organic solvent including an aromatic hydrocarbon such as benzene, toluene or xylene; an alcohol such as methanol, ethanol or n-propanol; an ether such as tetrahydrofuran or dioxane; an ester such as ethyl formate, methyl acetate, ethyl acetate, propyl acetate, butyl acetate or diethyl carbonate; or a mixed solvent such as mixtures of organic solvents or mixtures of water and one or more organic solvents thereof. Particularly, examples of preferable solvent used in the treatment with inorganic acid include mixtures of organic solvents selected from aromatic hydrocarbons, alcohols and esters listed above. Mixtures of organic solvents selected from alcohols and esters are more preferred, and a mixture of ethanol and butyl acetate is most preferred.

The reaction temperature and the reaction time mainly depend on the starting materials, solvent and acid or base used in the reaction, but are not particularly limited. The deprotection reaction is usually carried out at a temperature of from 0° C. to 150° C. for a period of from 1 to 20 hours in order to minimize the occurrence of side reactions.

Where the $R^1$ group is an aralkyl group or an aralkyloxycarbonyl group, the protective group is usually and preferably removed by treating with a reducing agent in a solvent (preferably by a catalytic hydrogenation with catalyst at room temperature) or by treating with an oxidizing agent.

There is no limitation on the solvent used in the deprotection reaction by the catalytic hydrogenation provided that it has no adverse effect on the reaction. Examples of preferable solvents include an alcohol such as methanol, ethanol or isopropanol; an ether such as diethyl ether, tetrahydrofuran or dioxane; an aromatic hydrocarbon such as toluene, benzene or xylene; an aliphatic hydrocarbon such as hexane or cyclohexane; an ester such as ethyl acetate or propyl acetate; an aliphatic acid such as acetic acid; or a mixture of water and one or more organic solvents thereof.

There is no limitation on the catalyst used in the deprotection reaction provided that it is usually used in catalytic hydrogenation reactions. Examples of preferable catalysts used in the catalytic hydrogenation include palladium on charcoal, Raney nickel, platinum oxide, platinum black, rhodium-aluminium oxide, triphenylphosphine-rhodium chloride and palladium-barium sulfate.

The pressure in the catalytic hydrogenation is not particularly limited, but the deprotection by the catalytic hydrogenation is usually carried out at a pressure of from 1 to 10 atmospheres.

The reaction temperature and the reaction time mainly depend on the starting materials, nature of the catalyst and solvent used in the reaction. The deprotection reaction is usually carried out at a temperature of from 0° C. to 100° C. for a period of from 5 minutes to 24 hours.

There is no limitation on the solvent used in the deprotection by oxidation reaction provided that it has no adverse effect on the reaction. This reaction is preferably carried out in an organic solvent containing water.

Examples of the preferable organic solvent used in this reaction include a ketone such as acetone; a halogenated hydrocarbon such as dichloromethane, chloroform or carbon tetrachloride; a nitrile such as acetonitrile; an ether such as diethyl ether, tetrahydrofuran or dioxane; an amide such as dimethylformamide, dimethylacetamide or hexamethylphosphoric triamide; or a sulfoxide such as dimethyl sulfoxide.

The oxidizing agent used in this reaction is not particularly limited provided that it is usually used for oxidation reactions. Examples of the preferable oxidizing agents used in this reaction include potassium persulfate, sodium persulfate, ammonium cerium nitrate (CAN) and 2,3-dichloro-5,6-dicyano-p-benzoquinone (DDQ).

The reaction temperature and the reaction time mainly depend on the starting materials, the nature of the oxidizing agent or the solvent used in the reaction. The deprotection reaction is usually carried out at a temperature of from 0° C. to 150° C. for a period of from 10 minutes to 24 hours.

Where the $R^1$ group is an alkenyloxycarbonyl group, the deprotection reaction is usually carried out by treating with a base under the same reaction conditions as that described for the deprotection of the amino group protected with the aliphatic acyl group, the aromatic acyl group or the alkoxycarbonyl group.

Where the $R^1$ group is an allyloxycarbonyl group, however, the deprotection is commonly carried out using palladium/triphenylphosphine or nickel tetracarbonyl, since this deprotection procedure is simple and the occurrence of side reactions can be prevented.

After the reaction is completed, the compound (IX) that is the desired product of this reaction is isolated from the reaction mixture using conventional techniques.

For example, the reaction mixture is neutralized appropriately or precipitates, if present, are removed by filtration, and the neutralized reaction mixture or the filtrate of the reaction mixture is partitioned between an organic solvent such as ethyl acetate that is immiscible with water and water or the like. The separated organic layer containing the desired compound is washed with water, dried over anhydrous magnesium sulfate or the like and concentrated to give the desired product.

The product thus obtained can, if necessary, be isolated and purified by conventional techniques such as recrystallization, reprecipitation or procedures that are usually used for the isolation and purification of the organic compounds. Examples of the procedure mentioned above include adsorption column chromatography using a stationary phase such as silica gel, alumina or florisil composed of magnesium-silica gel; partition chromatography using a synthetic adsorbent such as Sephadex LH-20 (a product of Pharmacia Co., Ltd.), Amberlite XAD-11 (a product of Rohm & Haas Co., Ltd.) or Diaion HP-20 (a product of Mitsubishi Chemical Corporation); ion-exchange chromatography; normal and reversed phase liquid chromatography using silica gel or alkylated silica gel (high performance liquid chromatography is preferred); or a suitable combination of these procedures, and the desired compound can be isolated and purified by elution with appropriate solvent from the column used.

In the case that it is necessary to separate isomers, each of the isomers can be separated at an appropriate stage such as the end of each step mentioned above or the end of a desired step by performing the suitable separation/purification procedure mentioned above or combination thereof.

Step 7

In Step 7, a compound (III) is prepared by octylation of the amino group of compound (IX) in the presence of a base in a solvent.

There is no limitation on the reagent for octylation provided that it is usually used in octylation reactions. Examples of preferable reagents used in this reaction include an octyl halide such as octyl chloride, octyl bromide or octyl iodide. Octyl bromide is more preferred.

There is no limitation on the base used in the reaction provided that it is usually used as a base in organic chemistry. Examples of preferable bases include an alkali metal carbonate such as sodium carbonate, potassium carbonate or lithium carbonate; an alkali metal bicarbonate such as sodium bicarbonate, potassium bicarbonate or lithium bicarbonate; an alkali metal hydride such as lithium hydride, sodium hydride or potassium hydride; a metal alkoxide such as sodium methoxide, sodium ethoxide, potassium methoxide, potassium ethoxide, potassium t-butoxide, lithium methoxide or lithium ethoxide; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-t-butyl-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo [5.4.0]undec-7-ene (DBU). An organic base is more preferred, and diisopropylethylamine is most preferred.

There is no limitation on the solvent used in the above-mentioned reaction provided that it has no adverse effect on the reaction and dissolves the starting materials to some extent. Examples of preferable solvents include an aromatic hydrocarbon such as benzene, toluene or xylene; an ester such as ethyl formate, methyl acetate, ethyl acetate, propyl acetate, butyl acetate or diethyl carbonate; an amide such as formamide, N,N-dimethylformamide, N,N-dimethylacetamide, N-methyl-2-pyrrolidone, N-methylpyrrolidinone, or hexamethylphosphoric triamide; or a sulfoxide such as dimethyl sulfoxide or sulfolane. Of these, aromatic hydrocarbons or esters are more preferred, further butyl acetate, toluene and xylene are still more preferred, and butyl acetate or xylene is most preferred.

The reaction temperature is usually from 0° C. to 160° C., and is preferably from 100° C. to 150° C.

The reaction time depends mainly on the reaction temperature, starting materials, and nature of the base or solvent used in the reaction. The reaction time is usually from 2 hours to one day and preferably from 4 hours to 10 hours.

After the reaction is completed, the compound (III) that is the desired product of this reaction is isolated from the reaction mixture using conventional techniques.

For example, the reaction mixture is neutralized appropriately or precipitates, if present, are removed by filtration, and the neutralized reaction mixture or the filtrate of the reaction mixture is partitioned between an organic solvent such as ethyl acetate that is immiscible with water and water or the like. The separated organic layer containing the desired compound is washed with water, dried over anhydrous magnesium sulfate or the like and concentrated to give the desired product.

The product thus obtained can, if necessary, be isolated and purified by conventional techniques such as recrystallization, reprecipitation or procedures that are usually used for the isolation and purification of the organic compounds. Examples of the procedure mentioned above include adsorption column chromatography using a stationary phase such as silica gel, alumina or florisil composed of magnesium-silica gel; partition column chromatography using a synthetic adsorbent such as Sephadex LH-20 (a product of Pharmacia Co., Ltd.), Amberlite XAD-11 (a product of Rohm & Haas Co., Ltd.) or Diaion HP-20 (a product of Mitsubishi Chemical Corporation); ion-exchange chromatography; normal and reversed phase liquid chromatography using silica gel or alkylated silica gel (high performance liquid chromatography is preferred); or a suitable combination of these procedures, and the desired compound can be isolated and purified by elution with appropriate solvent from the column used.

In the case that it is necessary to separate isomers, each of the isomers can be separated at an appropriate stage such as the end of each step mentioned above or the end of a desired step by performing the suitable separation/purification procedure mentioned above or combination thereof.

Step 8

In Step 8, a compound (1) that is a compound useful as an ACAT inhibitor is prepared by removing the $R^4$ group of the compound (III) and then converting to a sulfate derivative.

The procedures for removing the $R^4$ group depend on the nature of the protective group used, but the removal of the protective group is generally carried out according to procedures publicly known in the art as described below.

Where the $R^4$ group is a lower alkyl group or aryl group, the deprotection reaction is usually carried out by treating with an acid or a base.

Examples of preferable acids used in the above-mentioned reaction include hydrochloric acid, sulfuric acid, phosphoric acid or hydrobromic acid.

There is no limitation on the base used in the above-mentioned reaction provided that it has no adverse effect on the structural moieties other than the protective group. Examples of preferable bases include an alkali metal carbonate such as sodium carbonate or potassium carbonate; an organic base such as diisopropylethylamine; alkali metal hydroxides such as sodium hydroxide or potassium hydroxide; or concentrated ammonia solution in methanol.

There is no limitation on the solvent used in the above-mentioned reaction provided that it is usually used in hydrolysis reactions and has no adverse effect on the reaction. Examples of preferable solvents include water or a mixture of water and one or more organic solvents including an alcohol such as methanol, ethanol or n-propanol or an ether such as tetrahydrofuran or dioxane.

The reaction temperature and the reaction time depend mainly on starting materials, solvent and reagent used in the reaction, but are not particularly limited. The deprotection reaction is usually carried out at a temperature of from 0° C. to 150° C. for a period of from 1 to 10 hours in order to minimize the occurrence of side reactions.

Where the $R^4$ group is a diaryl-substituted methyl group such as diphenylmethyl group, the deprotection reaction is usually carried out by treating with an acid in a solvent.

Examples of preferable solvents used in the above-mentioned reaction include an aromatic hydrocarbon such as anisole. On the other hand, examples of preferable acids used in the above-mentioned reaction include a fluorinated organic acid such as trifluoroacetic acid.

The reaction temperature and the reaction time depend mainly on starting materials, solvent and acid used in the reaction. The reaction is usually carried out at room temperature for a period of from 30 minutes to 10 hours.

Where the $R^4$ group is an aralkyl group or a halogeno lower alkyl group, the deprotection reaction is usually carried out by a reduction reaction in a solvent.

Generally, when the protective group of the carboxyl group is a halogeno lower alkyl group, a chemical reduction such as a reduction reaction using zinc-acetic acid is preferable as the deprotection reaction. On the other hand, when the protective group of the carboxyl group is an aralkyl group, the deprotection is preferably carried out by conducting either a catalytic hydrogenation using catalysts such as palladium on charcoal or platinum or a chemical reduction using an alkali metal sulfide such as potassium sulfide or sodium sulfide.

There is no limitation on the solvent used in the above-mentioned reaction provided that it has no adverse effect on the reaction. Examples of preferable solvent include an alcohol such as methanol or ethanol; an ether such as tetrahydrofuran or dioxane; an aliphatic acid such as acetic acid; or a mixture of water and one or more organic solvents thereof.

The reaction temperature and the reaction time depend mainly on starting materials, solvent and reducing procedure used in the reaction. The deprotection reaction is usually carried out at a temperature of from 0° C. to room temperature for a period of from 5 minutes to 12 hours.

Where the $R^4$ group is an alkoxymethyl group, the protective group is usually removed by treating with an acid in a solvent.

There is no limitation on the acid used in this reaction provided that it is usually used as a Brønsted acid. Examples of preferable Brønsted acids include an inorganic acid such as hydrochloric acid or sulfuric acid; and an organic acid such as acetic acid or p-toluenesulfonic acid.

There is no limitation on the solvent used in the above-mentioned reaction provided that it has no adverse effect on the reaction. Examples of preferable solvents include an alcohol such as methanol or ethanol; an ether such as tetrahydrofuran or dioxane; or a mixture of water and one or more organic solvents thereof.

The reaction temperature and the reaction time depend mainly on starting materials, solvent and nature of the acid used in the reaction. The deprotection reaction is usually carried out at a temperature of from 0° C. to 50° C. for a period of from 10 minutes to 18 hours.

After the reaction is completed, the compound (1) that is the desired product of this reaction is isolated from the reaction mixture using conventional techniques.

For example, the reaction mixture is neutralized appropriately or precipitates, if present, are removed by filtration, and the neutralized reaction mixture or the filtrate of the reaction mixture is partitioned between an organic solvent such as ethyl acetate that is immiscible with water and water or the like. The separated organic layer containing the desired compound is washed with water, dried over anhydrous magnesium sulfate or the like and concentrated to give the desired product.

The product thus obtained can, if necessary, be isolated and purified by conventional techniques such as recrystallization, reprecipitation or procedures that are usually used for the isolation and purification of the organic compounds. Examples of the procedure mentioned above include adsorption column chromatography using a stationary phase such as silica gel, alumina or florisil composed of magnesium-silica gel; partition column chromatography using a synthetic adsorbent such as Sephadex LH-20 (a product of Pharmacia Co., Ltd.), Amberlite XAD-11 (a product of Rohm & Haas Co., Ltd.) or Diaion HP-20 (a product of Mitsubishi Chemical Corporation); ion-exchange chromatography; normal and reversed phase liquid chromatography using silica gel or alkylated silica gel (high performance liquid chromatography is preferred); or a suitable combination of these procedures, and the desired compound can be isolated and purified by elution with appropriate solvent from the column used.

The novel intermediates of this invention are useful products for manufacturing the above-mentioned indoline derivatives (1) having excellent ACAT inhibitory activity, and the novel manufacturing methods of this invention are superior to the publicly known conventional methods in respect of several points described below.

(1) there is no need to use bromine or sodium cyanide, which have some handling and safety problems in work operation, (2) operation conditions of reactions can be improved, especially, for example, in the nitration process, (3) productivity, such as being able to shorten working time (about ⅔), can be increased, (4) reaction conditions can be greatly relaxed, such as by lowering the concentration of aqueous sodium hydroxide solution in the last step of preparing the carboxylic acid compound, and (5) a high yield of the compound of formula (1) can be obtained (the previous overall yield of the compound of formula (1) from the compound of formula (2) disclosed in the prior art reference was 7.2%, whereas the yield obtained by this invention is 27.3% or more).

EXAMPLES

The following examples are intended to further illustrate the present invention and are not intended to limit the scope of the invention in any way.

Example 1

Preparation of hydroxy(1-acetyl-4,6-dimethylindolin-5-yl)acetic acid

To a suspension of 1-acetyl-4,6-dimethylindoline (50 g) in concentrated hydrochloric acid (400 ml) was added glyoxylic acid monohydrate (48.6 g, 2.0 equivalent), and the resulting mixture was stirred for 4.5 hours at 60° C. to 65° C. After cooling to 0° C. to 5° C., the reaction mixture was stirred further for more than 0.5 hours at this temperature, and crystals precipitated were separated by filtration and washed with water (500 ml).

The crystals obtained (about 126.4 g, wet weight) were dissolved in 1M aqueous sodium hydroxide solution (800 ml) under stirring, and the resulting mixture was washed with dichloromethane (700 ml). To the aqueous layer obtained was added methanol (700 ml), and the resulting mixture was adjusted to pH 2 by adding dropwise 1M hydrochloric acid (about 500 ml) with stirring while keeping the temperature at 0° C. to 5° C. After the resulting mixture was furthermore stirred for more than 0.5 hours under cooling, only methanol was evaporated off in vacuo. To the suspension thus obtained was added methanol (130 ml, methanol was added to adjust a ratio of water/methanol to 10/1), and the resulting mixture was stirred for more than 0.5 hours at 0° C. to 5° C.

Crystals precipitated were separated by filtration, washed with water (800 ml) and dried under reduced pressure (for more than 10 hours at 40° C.). At the end of this time, the dried crystals were taken out from the dryer and ground well and then further dried under reduced pressure (for more than 10 hours at 40° C.) to afford the title compound (59.8 g, yield: 86%) as colourless crystals.

$^1$H-NMR (DMSO-$d_6$) δ ppm 7.70 (1H, singlet); 5.33 (1H, singlet); 4.04 (2H, triplet, J=8.28 Hz); 2.99 (2H, triplet, J=8.28 Hz); 2.27 (3H, singlet); 2.16 (3H, singlet); 2.12 (3H, singlet).

Example 2

Preparation of 1-acetyl-5-ethoxycarbonylmethyl-4,6-dimethylindoline

To hydroxy(1-acetyl-4,6-dimethylindolin-5-yl)acetic acid (3.0 g) obtained in Example 1 and 7.5% palladium on charcoal (1.3 g, wet (water content: 53.1%)) placed in a 100-ml autoclave was added a saturated solution of hydrogen chloride in ethanol (30 ml). After degassing with nitrogen for 3 times (5 kg/cm$^2$ for each) and replacing nitrogen with hydrogen for 3 times (5 kg/cm$^2$ for each) successively, the resulting mixture was stirred for 5 hours at 70° C. under a pressurized hydrogen atmosphere (5 kg/cm$^2$). The reaction mixture was filtered to remove palladium on charcoal, which was washed with ethanol (45 ml). The filtrate and washing were combined and concentrated in vacuo, and after adding acetone (30 ml) to the residue, the resulting mixture was concentrated in vacuo once again. Subsequently, to the residue obtained were added acetone (30 ml), diisopropylethylamine (4.4 g, 3.0 equivalent) and acetyl chloride (0.81 ml, 1.0 equivalent) successively, and the resulting mixture was refluxed for 10 minutes. The reaction mixture was concentrated in vacuo. To the residue obtained were added water (30 ml) and ethyl acetate (60 ml) successively, and after stirring, the resulting mixture was filtered to remove insoluble precipitates, which were washed with water (30 ml) and ethyl acetate (30 ml) successively. The filtrate and washing were combined, and both organic and aqueous layers were separated by partitioning. The separated aqueous layer was extracted with ethyl acetate (30 ml) once again, and the extract was combined with the organic layer separated above. The organic layer was washed with water (30 ml), dried over anhydrous magnesium sulfate and concentrated under reduced pressure to afford the title compound (2.86 g, yield: 91%) as colourless crystals.

$^1$H-NMR (CDCl$_3$) δ ppm 7.93 (1H, singlet); 4.11 (2H, quartet, J=7.08 Hz); 4.01 (2H, triplet, J=8.28 Hz); 3.62 (2H, singlet); 3.07 (2H, triplet, J=8.28 Hz); 2.29 (3H, singlet); 2.18 (3H, singlet); 2.17 (3H, singlet); 1.21 (3H, triplet, J=7.08 Hz).

Example 3

Preparation of 1-acetyl-5-methoxycarbonylmethyl-4,6-dimethylindoline

The title compound was obtained as colourless crystals (yield: 82%) in similar manner to that mentioned in Example 2, using a saturated solution of hydrogen chloride in methanol as the reaction solvent in the place of the saturated solution of hydrogen chloride in ethanol.

¹H-NMR (CDCl₃) δ ppm 7.93 (1H, singlet); 4.02 (2H, triplet, J=8.28 Hz); 3.65 (3H, singlet); 3.64 (2H, singlet); 3.07 (2H, triplet, J=8.28 Hz); 2.29 (3H, singlet); 2.18 (3H, singlet); 2.17 (3H, singlet).

Example 4

Preparation of 1-acetyl-5-n-propyloxycarbonylmethyl-4,6-dimethylindoline

The title compound was obtained as colourless crystals (yield: 93%) in similar manner to that mentioned in Example 2, using a saturated solution of hydrogen chloride in n-propyl alcohol as the reaction solvent in the place of the saturated solution of hydrogen chloride in ethanol.

¹H-NMR (CDCl₃) δ ppm 7.92 (1H, singlet); 4.0 (4H, multiplet); 3.63 (2H, singlet); 3.06 (2H, triplet, J=8.28 Hz); 2.30 (3H, singlet); 2.17 (6H, singlet); 1.60 (2H, multiplet); 0.87 (3H, triplet, J=7.32 Hz).

Example 5

Preparation of 1-acetyl-7-nitro-5-ethoxycarbonylmethyl-4,6-dimethylindoline

To a solution of 1-acetyl-5-ethoxycarbonylmethyl-4,6-dimethylindoline prepared in the Example 2 (3.0 g) in acetic acid (30 ml) was added dropwise concentrated sulfuric acid (10.8 ml) with stirring under cooling in an ice-bath while keeping the reaction temperature below 20° C.

Subsequently, to the resulting mixture was added dropwise fuming nitric acid (0.81 ml, 1.8 equivalent) at −5° C., and the resulting mixture was stirred for 1 hour at this temperature. The reaction mixture was poured into cold water (90 ml) and twice extracted with dichloromethane (60 ml each). The combined organic layer was washed with a saturated aqueous sodium hydrogen carbonate solution (60 ml), 5% aqueous sodium hydrogen carbonate solution (60 ml) and water (60 ml) successively, dried over anhydrous magnesium sulfate and concentrated under reduced pressure to afford the title compound (3.17 g, yield: 91%) as colourless crystals.

¹H-NMR (CDCl₃) δ ppm 4.13 (2H, quartet, J=7.08 Hz); 4.13 (2H, triplet, J=8.04 Hz); 3.68 (2H, singlet); 2.28 (3H, singlet); 2.23 (3H, singlet); 2.21 (3H, singlet); 1.23 (3H, triplet, J=7.08 Hz).

Example 6

Preparation of 1-acetyl-7-nitro-5-methoxycarbonylmethyl-4,6-dimethylindoline

The title compound was obtained as colourless crystals (yield: 93%) in a similar manner to that mentioned in Example 5, using 1-acetyl-5-methoxycarbonylmethyl-4,6-dimethylindoline obtained in Example 3 as the starting material.

¹H-NMR (CDCl₃) δ ppm 4.14 (2H, triplet, J=8.04 Hz); 3.70 (2H, singlet); 3.67 (3H, singlet); 3.07 (2H, triplet, J=7.84 Hz); 2.28 (3H, singlet); 2.23 (3H, singlet); 2.21 (3H, singlet).

Example 7

Preparation of 1-acetyl-7-amino-5-ethoxycarbonylmethyl-4,6-dimethylindoline

In a 100-ml autoclave, 1-acetyl-7-nitro-5-ethoxycarbonylmethyl-4,6-dimethylindoline (5.0 g) obtained in Example 5 and 7.5% palladium on charcoal (wet, 3.76 g) were suspended in ethanol (50 ml). After degassing with nitrogen for 3 times (5 kg/cm² for each) and replacing nitrogen with hydrogen for 3 times (5 kg/cm² for each) successively, the resulting mixture was stirred for 2 hours at 55° C. under a pressurized hydrogen atmosphere (5 kg/cm²). The reaction mixture was filtered to remove palladium on charcoal, which was washed with ethanol (50 ml). The filtrate and washing were combined and concentrated under reduced pressure to give a fraction of the title compound. Furthermore, palladium on charcoal separated above was suspended in dichloromethane (50 ml), and after stirring at room temperature, the catalyst was removed by filtration and washed with dichloromethane (25 ml). The filtrate and washing were combined and concentrated under reduced pressure to give another fraction of the title compound. The title compound (4.1 g, yield: 90%) was obtained by combining two fractions of the title compound obtained above.

¹H-NMR (CDCl₃) δ ppm 4.10 (2H, quartet, J=7.08 Hz); 4.02 (2H, triplet, J=7.56 Hz); 3.64 (2H, singlet); 2.96 (2H, triplet, J=7.56 Hz); 2.29 (3H, singlet); 2.14 (3H, singlet); 2.14 (3H, singlet); 1.21 (3H, triplet, J=7.08 Hz).

Example 8

Preparation of 1-acetyl-7-amino-5-methoxycarbonylmethyl-4,6-dimethylindoline

The title compound was obtained in 93% yield in a similar manner to that mentioned in Example 7, using 1-acetyl-7-nitro-5-methoxycarbonylmethyl-4,6-dimethylindoline obtained in Example 6 as the starting material and methanol as the reaction solvent.

¹H-NMR (CDCl₃) δ ppm 4.02 (2H, triplet, J=7.8 Hz); 3.68 (2H, singlet); 3.64 (3H, singlet); 2.96 (2H, triplet, J=7.8 Hz); 2.29 (3H, singlet); 2.13 (6H, singlet).

Example 9

Preparation of N-(1-acetyl-5-ethoxycarbonylmethyl-4,6-dimethylindolin-7-yl)-2,2-dimethylpropanamide To a solution of 1-acetyl-7-amino-5-ethoxycarbonylmethyl-4,6-dimethylindoline obtained in Example 7 (4.0 g) in dichloromethane (40 ml) was added diisopropylethylamine (2.14 g, 1.2 equivalent) with stirring, and the resulting mixture was cooled to 0–5° C. Subsequently, to the reaction mixture was added dropwise pivaloyl chloride (1.74 g, 1.05 equivalent) at 0–5° C., and the resulting mixture was stirred for 1.0 hour at this temperature. The reaction mixture was washed with water (40 ml), and the resulting mixture was partitioned. The separated organic layer was washed twice with a saturated sodium hydrogen carbonate solution (20 ml each) and concentrated under reduced pressure. To the residue obtained was added ethyl acetate (20 ml), and the resulting mixture was concentrated under reduced pressure to about 12 ml. This addition and evaporation of ethyl acetate was repeated once again, and the resulting mixture was stirred at room temperature. After stirring, ethylcyclohexane (28 ml) was added, and the resulting mixture was stirred for more than 10 minutes at room temperature and then for more than 30 minutes at 0–5° C. Crystals precipitated were separated by filtration, washed with a mixed solvent of ethyl acetate and ethylcyclohexane (1:4)(40 ml) and dried under reduced pressure (50° C.) to afford the title compound (3.92 g, yield: 76%) as colourless crystals.

¹H-NMR (CDCl₃) δ ppm 9.18 (1H, singlet); 4.16 (1H, broad singlet); 4.11 (2H, quartet, J=7.08 Hz); 4.00 (1H, broad singlet); 3.68 (2H, doublet-like); 3.15 (1H, broad singlet); 2.84 (1H, broad singlet); 2.28 (3H, singlet); 2.17 (3H, singlet); 2.11 (3H, singlet); 1.25 (9H, singlet); 1.21 (3H, triplet, J=7.08 Hz).

Example 10

Preparation of N-(1-acetyl-5-methoxycarbonylmethyl-4,6-dimethylindolin-7-yl)-2,2-dimethylpropanamide The title compound was obtained as crystals in 98% yield in a similar manner to that mentioned in Example 9, using 1-acetyl-7-amino-5-methoxycarbonylmethyl-4,6-dimethylindoline obtained in Example 8 as the starting material.

$^1$H-NMR (CDCl$_3$) δ ppm 9.18 (1H, singlet); 4.16 (1H, broad singlet); 4.01 (1H, broad singlet); 3.70 (2H, doublet, J=12.2 Hz); 3.15 (1H, broad singlet); 2.85 (1H, broad singlet); 2.28 (3H, singlet); 2.16 (3H, singlet); 2.11 (3H, singlet); 1.25 (9H, singlet).

Example 11

Preparation of N-(5-ethoxycarbonylmethyl-4,6-dimethylindolin-7-yl)-2,2-dimethylpropanamide To a mixture of N-(1-acetyl-5-ethoxycarbonylmethyl-4,6-dimethylindolin-7-yl)-2,2-dimethylpropanamide obtained in Example 9 (3.5 g) and ethanol (35 ml) was added dropwise sodium ethoxide (20 wt % ethanol solution) while keeping the reaction temperature below 30° C., and the resulting mixture was refluxed for 1 hour. After cooling to 0–5° C., concentrated sulfuric acid (6.88 g, 7.5 equivalent) was added dropwise with stirring under cooling condition while keeping the reaction temperature below 30° C., and the resulting mixture was refluxed for 2 hours. Water (17.5 ml) was added to the reaction mixture, and ethanol was evaporated off in vacuo. To the residue obtained was added ethyl acetate (35 ml), and pH of the resulting mixture was adjusted with 25% aqueous sodium hydroxide solution (the aqueous layer was adjusted to pH 12–13), and the resulting mixture was partitioned between ethyl acetate and water. The separated organic layer was furthermore washed with water (35 ml). The washing and the aqueous layer separated above were combined and reextracted with ethyl acetate (35 ml). The extract and the organic layer separated above were combined and concentrated under reduced pressure to afford the title compound (3.26 g) as a crude product.

The physico-chemical properties of the title compound obtained were the same as those of the product obtained in the step (4) of Example 3 described in the Japanese Patent Number 2968050.

Example 12

Preparation of N-(5-methoxycarbonylmethyl-4,6-dimethylindolin-7-yl)-2,2-dimethylpropanamide The title compound was obtained in 83% yield in a similar manner to that mentioned in Example 11, using N-(1-acetyl-5-methoxycarbonylmethyl-4,6-dimethylindolin-7-yl)-2,2-dimethylpropanamide obtained in Example 10 and sodium methoxide as the starting materials and methanol as the reaction solvent.

$^1$H-NMR (CDCl$_3$) δ ppm 7.05 (1H, singlet); 3.64 (2H, singlet); 3.61 (2H, singlet); 3.53 (2H, triplet, J=8.56 Hz); 2.99 (2H, triplet, J=8.56 Hz); 2.16 (3H, singlet); 2.13 (3H, singlet); 1.33 (9H, singlet).

Example 13

Preparation of N-(5-carboxymethyl-4,6-dimethyl-1-octylindolin-7-yl)-2,2-dimethylpropanamide sulfate To N-(5-ethoxycarbonylmethyl-4,6-dimethylindolin-7-yl)-2,2-dimethylpropanamide obtained in Example 11 (2.8 g) were added xylene (28 ml), diisopropylethylamine (1.72 ml, 1.2 equivalent) and 1-octyl bromide (1.80 ml, 1.3 equivalent), and the resulting mixture was refluxed for more than 8 hours. After cooling to below 70° C., water (28 ml) was added, and the resulting mixture was partitioned. The separated organic layer was furthermore washed twice with water (28 ml each) and concentrated in vacuo until the volume of xylene was reduced to about 6 ml to give a solution of the title compound in xylene. To a mixture of the solution of the title compound in xylene and 90% aqueous ethanol solution (28 ml) was added sodium hydroxide (1.66 g, 5.0 equivalent), and the resulting mixture was stirred for 1 hour at the reaction temperature of 80° C. After cooling to below 30° C., water (15.5 ml) was added, and the resulting mixture was concentrated in vacuo until the volume of the solution was reduced to 18 ml. Subsequently, acetone (15.5 ml) was added to the residual solution, and the resulting mixture was adjusted to pH 1.4–1.6 with 4N sulfuric acid at room temperature. Furthermore, water was added to make a total volume of water of 46 ml, and the resulting mixture was stirred for more than 30 minutes at 25–30° C. (ambient temperature). After crystals were precipitated, only acetone was evaporated off in vacuo. To the residue was added acetone (5.0 ml), and the resulting mixture was stirred for more than 30 minutes at 25–30° C. (ambient temperature), and then crystals were separated by filtration. The crystals thus obtained were washed with 10% aqueous acetone solution and dried under reduced pressure to afford the title compound (2.88 g, yield: 86%) as crystals.

The physico-chemical properties of the title compound obtained were the same as those of the product obtained in Example 6 described in Japanese Patent Number 2968050.

Example 14

Preparation of N-(5-carboxymethyl-4,6-dimethyl-1-octylindolin-7-yl)-2,2-dimethylpropanamide sulfate To N-(5-methoxycarbonylmethyl-4,6-dimethylindolin-7-yl)-2,2-dimethylpropanamide obtained in Example 12 (2.3 g) were added xylene (23 ml), diisopropylethylamine (1.12 ml, 1.2 equivalent) and 1-octyl bromide (1.81 ml, 1.3 equivalent), and the resulting mixture was refluxed for more than 8.5 hours. After cooling to below 70° C., water (23 ml) was added, and the resulting mixture was partitioned. The separated organic layer was furthermore washed twice with water (10 ml each) and concentrated under reduced pressure to afford crystals. To the crystals obtained were added ethyl acetate (4 ml) and hexane (8 ml), and the resulting mixture was stirred for a while, and the crystals were separated by filtration.

Subsequently, to a solution of the crystal obtained above (1.7 g) in 75% aqueous methanol solution (37.4 ml) was added sodium hydroxide (0.79 g, 5.0 equivalent), and the resulting mixture was stirred for 1.5 hours in a bath controlled at 60° C. After cooling to below 30° C., methanol was evaporated off in vacuo, and to the residue was added acetone (9.3 ml), and then the resulting mixture was adjusted to pH 1.4–1.6 with 4N sulfuric acid at room temperature. Subsequently, water was added to make the total volume of water 38 ml, and the resulting mixture was stirred for more than 30 minutes at 25–30° C. (ambient temperature). After crystals were precipitated, only acetone was evaporated off in vacuo. To the residue was added acetone (5.0 ml), and the resulting mixture was stirred for more than 30 minutes at 25–30° C. (ambient temperature), and the crystals were separated by filtration. The crystals obtained were washed with 10% aqueous acetone solution and dried under reduced pressure to afford the title compound (1.72 g, yield: 56%) as crystals.

The physico-chemical properties of the title compound obtained were the same as those of the product obtained in Example 6 described in Japanese Patent Number 2968050.

Example 15

Preparation of (1-acetyl-4,6-dimethylindolin-5-yl)acetic acid

To a solution of hydroxy(1-acetyl-4,6-dimethylindolin-5-yl)acetic acid obtained in Example 1 (280 g) in acetic acid (1120 ml) were added phosphorous acid (130 g) and potassium iodide (17.6 g), and the resulting mixture was stirred for 2 hours at 100–107° C. After cooling to 50° C., water (1120 ml) was added, and crystals precipitated were separated by filtration and dried to afford (1-acetyl-4,6-dimethylindolin-5-yl)acetic acid (223 g, yield: 85%).

Melting point: No change was observed in its appearance by 250° C. $^1$H-NMR (DMSO-$d_6$) δ ppm 7.75 (1H, singlet); 4.02 (2H, triplet, J=8.0); 3.53 (2H, singlet); 2.98 (2H, triplet, J=8.0); 2.22 (3H, singlet); 2.12 (6H, singlet); IR spectrum (KBr)cm$^{-1}$:1715,1620.

Example 16

Preparation of 1-acetyl-5-ethoxycarbonylmethyl-4,6-dimethylindoline

To a solution of hydrogen chloride (665 g) in ethanol (2000 ml) was added (1-acetyl-4,6-dimethylindolin-5-yl)acetic acid obtained in Example 15 (150 g), and the resulting mixture was stirred for 30 minutes at 45–50° C., and then an ethanol fraction containing hydrochloric acid (1000 ml) was evaporated off in vacuo. At about 20° C., water (2000 ml) was added, and crystals precipitated were separated by filtration and dried to afford 1-acetyl-5-ethoxycarbonylmethyl-4,6-dimethylindoline (146 g, yield: 87%), of which the physico-chemical properties were the same as those of the product obtained in Example 2.

Example 17

Preparation of N-(5-ethoxycarbonylmethyl-4,6-dimethylindolin-7-yl)-2,2-dimethylpropanamide hydrochloride A solution of N-(1-acetyl-5-ethoxycarbonylmethyl-4,6-dimethylindolin-7-yl)-2,2-dimethylpropanamide prepared in Example 9 (20 g) in a mixed solvent of xylene (200 ml) and ethanol (40 ml) was stirred for 5.5 hours at 80–85° C. while bubbling hydrogen chloride gas (23.1 g) into the reaction solution. After cooling, xylene (200 ml) was added, and the resulting mixture was concentrated in vacuo until the total volume of the solution was reduced to about 200 ml. Subsequently, the residual solution was stirred for 0.5 hours at 0–5° C., and crystals precipitated were separated by filtration to afford the title compound (19.25 g, yield: 98%).

$^1$H-NMR (DMSO-$d_6$) δ ppm 9.39 (1H, singlet) 4.07 (2H, quartet, J=7.1 Hz) 3.77 (2H, singlet) 3.68 (2H, triplet, J=7.4 Hz) 3.17 (2H, triplet, J=7.4 Hz) 2.19 (3H, singlet) 2.07 (3H, singlet) 1.28 (9H, singlet) 1.17 (3H, triplet, J=7.1 Hz).

Example 18

Preparation of N-(5-ethoxycarbonylmethyl-4,6-dimethylindolin-7-yl)-2,2-dimethylpropanamide hydrochloride Into a solution of N-(1-acetyl-5-ethoxycarbonylmethyl-4,6-dimethylindolin-7-yl)-2,2-dimethylpropanamide prepared in Example 9 (20 g) in a mixed solvent of toluene (200 ml) and ethanol (40 ml) was bubbled hydrogen chloride gas (19.8 g) under sealed reaction conditions, and the resulting mixture was stirred for 10.5 hours at 80–85° C. After cooling, the reaction mixture was concentrated in vacuo until the total volume of the solution was reduced to about 140 ml, and crystals precipitated were separated by filtration to afford the title compound (18.1 g, yield: 92%).

The physico-chemical properties of the title compound obtained were the same as those of the product obtained in Example 17.

Example 19

Preparation of N-(5-ethoxycarbonylmethyl-4,6-dimethylindolin-7-yl)-2,2-dimethylpropanamide hydrochloride Into a solution of N-(1-acetyl-5-ethoxycarbonylmethyl-4,6-dimethylindolin-7-yl)-2,2-dimethylpropanamide prepared in Example 9 (50 g) in a mixed solvent of butyl acetate (400 ml) and ethanol (8.6 ml) was bubbled hydrogen chloride gas (7.3 g) under sealed reaction conditions, and the resulting mixture was stirred for 9.5 hours at 90–95° C. After cooling, the reaction mixture was concentrated in vacuo until the total volume of the solution was reduced to about 300 ml, and crystals precipitated were separated by filtration to afford the title compound (46.8 g, yield: 95%).

The physico-chemical properties of the title compound obtained were the same as those of the product obtained in Example 17.

Example 20

Preparation of N-(5-carboxymethyl-4,6-dimethyl-1-octylindolin-7-yl)-2,2-dimethylpropanamide sulfate To a suspension of N-(5-ethoxycarbonylmethyl-4,6-dimethylindolin-7-yl)-2,2-dimethylpropanamide hydrochloride obtained in Example 17 (49.3 g) in xylene (300 ml) were added diisopropylethylamine (34.5 g) and octyl bromide (51.6 g) successively, and the resulting mixture was stirred for 5 hours at 140–145° C. After cooling, the reaction mixture was washed with 3% aqueous sulfuric acid solution twice (150 ml each) and 5% aqueous sodium hydroxide solution (150 ml) successively. Subsequently, to the organic layer separated were added ethanol (75 ml) and 25% aqueous sodium hydroxide solution (36.5 g), and the resulting mixture was stirred for 3 hours at 50° C. After stirring, water (300 ml) was added, and the resulting mixture was stirred for 0.15 hours at room temperature. After partitioning the reaction mixture, the separated aqueous layer was concentrated in vacuo to remove ethanol, and to the residue was added acetone (75 ml), and then the resulting mixture was adjusted to pH 1.4–1.6 with sulfuric acid and seeded with crystals of authentic sample. After crystals were precipitated, water (300 ml) was added dropwise, and the resulting mixture was furthermore stirred for 1 hour at 0–5° C. Crystals precipitated were separated by filtration to afford a crude product of the title compound (58.9 g). Subsequently, the crude product of the title compound obtained above (20 g) was suspended in a mixed solvent of ethyl acetate (95 ml) and water (5 ml) and stirred for 3 hours at 40–50° C. and then for 1 hour at 0–5° C. Crystals precipitated were separated by filtration to afford the title compound (19.2 g, overall yield: 91%).

The physico-chemical properties of the title compound obtained were the same as those of the product obtained in Example 6 described in Japanese Patent Number 2968050.

Example 21

Preparation of N-(5-carboxymethyl-4,6-dimethyl-1-octylindolin-7-yl)-2,2-dimethylpropanamide sulfate Into a solution of N-(1-acetyl-5-ethoxycarbonylmethyl-4,6-dimethylindolin-7-yl)-2,2-dimethylpropanamide prepared in Example 9 (50 g) in a mixed solvent of butyl acetate (400 ml) and ethanol (8.6 ml) was bubbled hydrogen chloride gas (15.2 g) under sealed reaction conditions, and the resulting mixture was stirred for 9 hours at 70–75° C. After cooling, the reaction mixture was concentrated in vacuo until the total volume of the solution was reduced to about 300 ml. To the resulting mixture was added diisopropylethylamine (47 ml), octyl bromide (47 ml) and butyl acetate (50 ml) successively, and the resulting mixture was stirred for 9 hours at 130–135° C. After cooling, the reaction mixture was washed with 3% aqueous sulfuric acid solution twice (150 ml each) and 5% aqueous sodium hydrogen carbonate solution (300 ml) successively. The organic layer separated was concentrated in vacuo to remove the solvent, and to the residue were added ethanol (100 ml) and 25% aqueous sodium hydroxide solution (36.3 g), and the resulting mixture was stirred for 3 hours at 50–70° C. After stirring, water (300 ml) was added, and the resulting mixture was concentrated in vacuo to remove ethanol. To the residue were added water (200 ml) and acetone (200 ml), and the resulting mixture was adjusted to pH 1.4–1.6 with sulfuric acid and seeded with crystals of authentic product. After the crystals were precipitated, water (375 ml) was added dropwise and the resulting mixture was furthermore stirred for 1 hour at 0–5° C. Crystals precipitated were separated by filtration to afford a crude product of the title compound (57.1 g).

Subsequently, the crude product of the title compound obtained above (50 g) was suspended in a mixed solvent of ethyl acetate (235 ml) and water (12.5 ml) and stirred for 3 hours at 40–50° C. and then for 1 hour at 0–5° C. Crystals precipitated were separated by filtration to afford the title compound (48.6 g, overall yield: 88%).

The physico-chemical properties of the title compound obtained were the same as those of the product obtained in Example 6 described in Japanese Patent Number 2968050.

Example 22

Preparation of N-(5-carboxymethyl-4,6-dimethyl-1-octylindolin-7-yl)-2,2-dimethylpropanamide sulfate Into a solution of N-(1-acetyl-5-ethoxycarbonylmethyl-4,6-dimethylindolin-7-yl)-2,2-dimethylpropanamide prepared in Example 9 (50 g) in a mixed solvent of xylene (460 ml) and ethanol (8.4 ml) was bubbled hydrogen chloride gas (12.2 g) under sealed reaction conditions, and the resulting mixture was stirred for 8.5 hours at 70–75° C. After cooling, the reaction mixture was concentrated in vacuo until the total volume of the solution was reduced to about 350 ml. To the resulting mixture was added diisopropylethylamine (34.9 ml), octyl bromide (46 ml) and xylene (100 ml) successively, and the resulting mixture was stirred for 9 hours at 135–140° C. After cooling, the reaction mixture was washed with 3% aqueous sulfuric acid solution twice (150 ml each) and 5% aqueous sodium hydroxide solution (150 ml) successively. Subsequently, to the organic layer separated were added ethanol (125 ml) and 25% aqueous sodium hydroxide solution (42.7 g), and the resulting mixture was stirred for 1 hour at 70–80° C. After stirring, water (300 ml) was added, and the resulting mixture was stirred for 0.15 hours at room temperature. After partitioning the reaction mixture, the separated aqueous layer was concentrated in vacuo to remove ethanol, and to the residue were added water (200 ml) and acetone (200 ml), and the resulting mixture was adjusted to pH 1.4–1.6 with sulfuric acid and seeded with crystals of authentic product. After crystals were precipitated, water (375 ml) was added dropwise, and the resulting mixture was furthermore stirred for 1 hour at 0–5° C. Crystals precipitated were separated by filtration to afford a crude product of the title compound (53.1 g).

Subsequently, the crude product of the title compound obtained above (50 g) was suspended in a mixed solvent of ethyl acetate (237.5 ml) and water (12.5 ml) and stirred for 3 hours at 40–50° C. and then for 1 hour at 0–5° C. Crystals precipitated were separated by filtration to afford the title compound (47.5 g, overall yield: 81%).

The physico-chemical properties of the title compound obtained were the same as those of the product obtained in Example 6 described in Japanese Patent Number 2968050.

Example 23

Preparation of N-(5-carboxymethyl-4,6-dimethyl-1-octylindolin-7-yl)-2,2-dimethylpropanamide sulfate Into a solution of N-(1-acetyl-5-ethoxycarbonylmethyl-4,6-dimethylindolin-7-yl)-2,2-dimethylpropanamide prepared in Example 9 (50 g) in a mixed solvent of ethyl acetate (400 ml) and ethanol (8.6 ml) was bubbled hydrogen chloride gas (19.5 g) under sealed reaction conditions, and the resulting mixture was stirred for 9 hours at 60–65° C. The reaction mixture was concentrated in vacuo to remove ethyl acetate, and to the residue were added xylene (400 ml), diisopropylethylamine (58 ml) and octyl bromide (46 ml) successively, and the resulting mixture was stirred for 18 hours at 120–130° C. After cooling, the reaction mixture was washed with 3% aqueous sulfuric acid solution twice (150 ml each) and 5% aqueous sodium hydroxide solution (150 ml) successively. Subsequently, the organic layer separated was evaporated in vacuo to remove the solvents, and to the residue were added ethanol (450 ml) and 25% aqueous sodium hydroxide solution (36.3 g), and the resulting mixture was stirred for 3.5 hours at 50° C. Water (275 ml) was added, and the resulting mixture was concentrated in vacuo to remove ethanol. To the residue were added water (200 ml) and acetone (200 ml), and the resulting mixture was adjusted to pH 1.4–1.6 with sulfuric acid and seeded with crystals of authentic product. After the crystals were precipitated, water (375 ml) was added dropwise and the resulting mixture was furthermore stirred for 1 hour at 0–5° C. Crystals precipitated were separated by filtration to afford a crude product of the title compound (60.4 g). Subsequently, the crude product of the title compound obtained above (50 g) was suspended in a mixed solvent of ethyl acetate (238 ml) and water (12.5 ml) and stirred for 3 hours at 40–50° C. and then for 1 hour at 0–5° C. Crystals precipitated were separated by filtration to afford the title compound (46.4 g, overall yield: 90.2%).

The physico-chemical properties of the title compound obtained were the same as those of the product obtained in Example 6 described in Japanese Patent Number 2968050.

Example 24

Preparation of N-(5-carboxymethyl-4,6-dimethyl-1-octylindolin-7-yl)-2,2-dimethylpropanamide sulfate To N-(1-acetyl-5-ethoxycarbonylmethyl-4,6-dimethylindolin-7-yl)-2,2-dimethylpropanamide prepared in Example 9 (3 g) were added 1M solution of lithium ethoxide in ethanol (16.0 ml) and ethanol (2 ml), and the resulting mixture was stirred for 2.5 hours at 75–80° C. To the reaction mixture was added octyl bromide (4.64 g), and the resulting mixture was stirred for 21 hours at 85–90° C. To the reaction mixture was added 25% aqueous sodium hydroxide solution (6.41 g), and the resulting mixture was stirred for 1 hour at 80–85° C. After cooling to room temperature, toluene (18 ml), water (18 ml) and ethanol (3 ml) were added successively, and the resulting mixture was stirred. After partitioning the resulting mixture, the separated aqueous layer was concentrated in vacuo to remove ethanol. To the residue were added water (7.5 ml) and acetone (12 ml), and the resulting mixture was adjusted to pH 1.4–1.6 with sulfuric acid and seeded with crystals of authentic product. To the resulting mixture was added dropwise water (15 ml), and the resulting mixture was stirred for 1 hour at room temperature and then for 1 hour at 0–5° C. Crystals precipitated were separated by filtration to afford a crude product of the title compound (3.45 g). Subsequently, the crude product of the title compound obtained above (3 g) was suspended in a mixed solvent of ethyl acetate (14.3 ml) and water (0.75 ml) and stirred for 3 hours at 40–50° C. and then for 1 hour at 0–5° C. Crystals precipitated were separated by filtration to afford the title compound (2.77 g, overall yield: 85.3%).

The physico-chemical properties of the title compound obtained were the same as those of the product obtained in Example 6 described in Japanese Patent Number 2968050.

What is claimed is:

1. A synthetic intermediate of general formula (II)

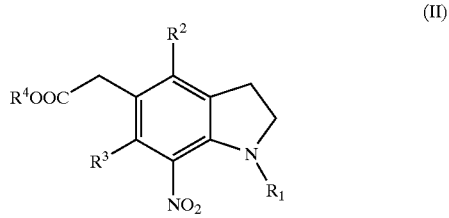

(II)

wherein $R^1$ represents a protective group for the amino group, $R^2$ and $R^3$ are the same or different and each represents a lower alkyl group, $R^4$ represents a hydrogen atom or a protective group for the carboxyl group; a salt or an amide derivative thereof.

* * * * *

UNITED STATES PATENT AND TRADEMARK OFFICE
CERTIFICATE OF CORRECTION

PATENT NO. : 7,012,147 B2 Page 1 of 1
APPLICATION NO. : 10/635040
DATED : March 14, 2006
INVENTOR(S) : Tomori et al It is certified that error appears in the above-identified patent and that said Letters Patent is hereby corrected as shown below:

Title Page, item, (73) Inventors: delete "Katsuhiko Fujimoto, Hiratsuka (JP); Masakazu Wakayama, Hiratsuka (JP); Motoko Miura, Hiratsuka (JP); and Kazuhiko Shimura, Isehara (JP)".

Signed and Sealed this

Twenty-fifth Day of July, 2006

JON W. DUDAS
*Director of the United States Patent and Trademark Office*